US008633160B2

(12) United States Patent
Belmares et al.

(10) Patent No.: US 8,633,160 B2
(45) Date of Patent: Jan. 21, 2014

(54) SMALL MOLECULE INHIBITORS OF PDZ INTERACTIONS

(75) Inventors: Michael P. Belmares, San Jose, CA (US); Kenneth A. Mendoza, Oakland, CA (US); Peter S. Lu, Palo Alto, CA (US); David Garman, San Jose, CA (US); Michael Tymianski, Toronto (CA)

(73) Assignee: Nono Inc. (CA)

( * ) Notice: Subject to any disclaimer, the term of this patent is extended or adjusted under 35 U.S.C. 154(b) by 1003 days.

(21) Appl. No.: 12/167,852

(22) Filed: Jul. 3, 2008

(65) Prior Publication Data
US 2009/0062213 A1 Mar. 5, 2009

Related U.S. Application Data

(63) Continuation-in-part of application No. PCT/US2006/062715, filed on Dec. 29, 2006.

(60) Provisional application No. 60/947,883, filed on Jul. 3, 2007, provisional application No. 60/693,988, filed on Jun. 23, 2005, provisional application No. 60/755,315, filed on Dec. 30, 2005.

(51) Int. Cl.
*A61K 38/00* (2006.01)
*A61P 25/00* (2006.01)

(52) U.S. Cl.
USPC ...................................... 514/17.7

(58) Field of Classification Search
None
See application file for complete search history.

(56) References Cited

U.S. PATENT DOCUMENTS

| 6,083,986 | A | 7/2000 | Castle et al. | 514/586 |
|---|---|---|---|---|
| 6,869,789 | B2 * | 3/2005 | Liu et al. | 435/232 |
| 6,942,981 | B1 | 9/2005 | Lu et al. | 435/7.1 |
| 7,312,041 | B2 | 12/2007 | Lu et al. | 435/7.1 |
| 7,517,998 | B2 | 4/2009 | Deroy et al. | 544/106 |
| 7,588,911 | B2 | 9/2009 | Belmares et al. | 435/25 |
| 2004/0018487 | A1 | 1/2004 | Lu et al. | |
| 2005/0164344 | A1 | 7/2005 | Worley et al. | |
| 2005/0164933 | A1* | 7/2005 | Tymianski et al. | 514/12 |
| 2005/0282907 | A1 | 12/2005 | Deroy et al. | |
| 2007/0014803 | A1 | 1/2007 | Lu et al. | 435/69.1 |
| 2007/0020717 | A1 | 1/2007 | Belmares et al. | |
| 2007/0185176 | A1 | 8/2007 | Van Gelder et al. | |
| 2008/0039456 | A1 | 2/2008 | Gelder et al. | |
| 2008/0227684 | A1 | 9/2008 | Belmares et al. | |

FOREIGN PATENT DOCUMENTS

| WO | WO 2004/009533 A1 | 1/2000 |
|---|---|---|
| WO | WO 02/31117 | 4/2002 |
| WO | WO 02/42422 | 5/2002 |
| WO | WO 03/014303 | 2/2003 |
| WO | WO 2004/022006 | 3/2004 |
| WO | WO 2004/045535 A2 | 6/2004 |
| WO | WO 2004045535 A2 * | 6/2004 |
| WO | WO 2004/092339 | 10/2004 |
| WO | WO 2005/016870 A1 | 2/2005 |
| WO | WO 2005/074375 A2 | 8/2005 |
| WO | WO 2005074375 A2 * | 8/2005 |
| WO | WO 2005/097090 A2 | 10/2005 |
| WO | WO 2007/002395 A1 | 1/2007 |
| WO | WO 2007002395 A1 * | 1/2007 |
| WO | WO 2007/079406 | 7/2007 |
| WO | WO 2009/006611 A1 | 1/2009 |

OTHER PUBLICATIONS

U.S. Appl. No. 12/771,511, filed Apr. 2010, Belmares et al.*
Aarts, "Treatment of ischemic brain damage by perturbing NMDA receptor- PSD-95 protein interactions," *Science*, 298: 846-850, 2002.
Boukerche et al., "mda-9/Syntenin: a positive regulator of melanoma metastasis," *Cancer Res.*, 65 (23): 10901-10911, 2005.
Deval et al., "Mechanistic insights into the suppression of drug resistance by human immunodeficiency virus type 1 reverse transcriptase using alpha-boranophosphate nucleoside analogs," *J. Biol. Chem.*, 280 (5): 3838-3846, 2005.
Du et al., "Association of cottontail rabbit papillomavirus E6 oncoproteins with the hD1g/SAP97 tumor suppressor," *J. Cell. Biochem.*, 94 (5): 1038-1045, 2005.
Garry, "Neuropathic sensitization of behavioral reflexes and spinal NMDA receptor/CaM kinase II interactions are disrupted in PSD-95 mutant mice," *Curr. Biol.*, 13: 321-328, 2003.
Hampson et al., "The PDZ protein Tip-1 is a gain of function target of the HPV16 E6 oncoprotein," *Int. J. Oncology*, 25 (5): 1249-1256, 2004.
Hirata et al., "PDZ domain-binding motif of human T-cell leukemia virus type 1 Tax oncoprotein augments the transforming activity in a rat fibroblast cell line," *Virology*, 318 (1): 327-336, 2004.
International Search Report and Written Opinion, in Int. App. No. PCT/US2008/69230, mailed Sep. 26, 2008.
Kanamori, "The PDZ protein tax-interacting protein-1 inhibits beta-catenin transcriptional activity and growth of colorectal cancer cells," *J. Biol. Chem.*, 278 (40): 38758-38764, 2003.
Latorre et al., "Viral oncoprotein-induced mislocalization of select PDZ proteins disrupts tight junctions and causes polarity defects in epithelial cells," *J. Cell Science*, 118 (Pt. 18): 4283-4293, 2005.
Roche, "The expanding role of PSD-95: a new link to addiction," *Trends Neurosci.*, 12: 699-700, 2004.
Sattler, "Specific coupling of NMDA receptor activation to nitric oxide neurotoxicity by PSD-95 protein," *Science*, 284 (5421): 1845-1848, 1999.
Shibata et al., "EBP50, a beta-catenin-associating protein, enhances Wnt signaling and is over-expressed in hepatocellular carcinoma," *Hepatology*, 38 (1): 178-186, 2003.
Tao et al., "Role of postsynaptic density protein-95 in the maintenance of peripheral nerve injury-induced neuropathic pain in rats," *Neuroscience*, 117 (3): 731-739, 2003.

(Continued)

*Primary Examiner* — Sreeni Padmanabhan
*Assistant Examiner* — Svetlana M Ivanova
(74) *Attorney, Agent, or Firm* — Alston & Bird LLP

(57) ABSTRACT

The present invention relates to compositions for use in the modulation of PDZ domain interactions with cognate ligands. Methods of assessing and characterizing PDZ domain interactions from various polypeptides also are provided.

11 Claims, 11 Drawing Sheets

(56) References Cited

OTHER PUBLICATIONS

Xie et al., "PDZ binding motif of HTLV-1 Tax promotes virus-mediated T-cell proliferation in vitro and persistence in vivo," *Blood*, 107(5): 1980-1988, 2005.
Yao, "Identification of PSD-95 as a regulator of dopamine-mediated synaptic and behavioral plasticity," *Neuron*, 41 (4): 625-638, 2004.
Antoniv et al., "Identification of Repressor in the First Intron of the Human a2(I) Collagen Gene (COL1A2)," *J. Biol. Chem.*, 280(42):35417-35423, 2005.
"Cancer Pain" Publication review Stanley Swerzewski,1999.
Hewett et al., "Cyclooxygenase-2 contributes to N-methyl-D-aspartate-mediated neuronal cell death in primary cortical cell culture," *The Journal of Pharamacology and Experimental Therapeutics*, 293(2): 417-425 (2000).
Hixson et al., "Antiproliferative effect of NSAIDs agianst Human colon cancer cells," *Cancer Epidemiology, Biomarkers and Prevention*, 3(5): 433-438 (1994).
International Preliminary Examination Report mailed Jul. 4, 2007 for Application PCT/US2003/036698.
International Search Report mailed Nov. 14, 2006 for application PCT/US/06/24475 (WO 2007/002395 A1).
International Search Report mailed Jul. 12, 2007 for application PCT/US2006/062715.
International Search Report mailed Jan. 8, 2009 for application PCT/US2008/069230.
International Preliminary Report on Patentability (Chapter I) and Written Opinion Completed Jul. 1, 2008 for PCT/US2006/062715.
International Preliminary Report on Patentability (Chapter I) and Written Opinion Completed Jan. 5, 2010 for PCT/US2008/069230.
Iwamoto et al., "Differential modulation of NR1-NR2A and NR1-NR2B subtypes of NMDA receptor by PDZ Domain-containing proteins," *J. Neurochem.*, 89:100-108, (2004).
Jaffrey et al., "CAPON: A Protein Associated with Neuronal Nitric Oxide Synthase that Regulates its interaction with PSD-95", *Neuron*, 20:115-124, (1998).
Kardosh et al., "Differential Effects of Selective COX-2 inhibitors on cell cycle regulation and proiferation of glioblastoma cell lines", *Cancer Biol. Ther.*, 3(1);55-62, (2004).
Komau et al., "Domain interactions between NMDA receptor subunits and the postsyanptic density protein, PSD-95", *Science*, 269:1737-1740, (1995).
Kreienkamp et al., "The calcium-independent receptor for alpha-latrotoxin from human and rodent brains interacts with members of the proSAP/SSTRIP/Shank family of multidomain proteins", *J. Biol. Chem.*, 275(42):32387-32390, (2000).
Laura et al., "MAG1-1: a wide expressed, alternatively spliced tight junction protein", *Exp. Cell Res.*, 275:155-170, (2002).
Leasge et al., "Cancer Control" *Journal of the Moffitt Cancer* 1999:6(20):136-145.
Saibo et al., "Stress and mitogen-induced phosphorylation of the synapse-associated protein SAP90/PSD-95 by activation of SAPK3/p38-gamma and ERK1/ERK2", *Biochem J.*, 380:19-30, (2004).
Saras et al., "PDZ domains bind carboxyl-terminal sequence of target proteins," *Trends in Biochemical Sciences*, 21(12): 455-458 (1996).
Schwarze et al., "In vivo Protein Transduction: Delivery of Biologically active Protein into mouse", *Science*, 258:1569-1572, (1999).

Supplementary Partial European Search Reort mailed Dec. 9, 2008 for Application 06785433.1.
Songyang et al., "Recognition of Unique Carboxyl-Terminal Motifs by Distinct PDZ Domains," *Science* 275 (5296): 73-77, 1997.
Tang et al., "Flavonoids from Radix scutellariae as potential stroke therapeutic agents by targeting the second postsynaptic density 95(PSD-95)/disc large/zonula occludens-1 (PDZ) domain of PSD-95", *Phytomedicine* 11(4): 277-284, (2004).
U.S. Appl. No. 11/426,282, Notice of Allowance mailed May. 11, 2009.
U.S. Appl. No. 11/426,282, Notice of Allowance mailed Apr. 7, 2009.
U.S. Appl. No. 11/426,282, Office Action mailed Nov. 17, 2008.
U.S. Appl. No. 11/426,282, Restriction Requirement mailed Jun. 30, 2008.
U.S. Appl. No. 11/618,092, Office Action mailed Nov. 2, 2009.
U.S. Appl. No. 11/618,092, Restriction Requirement mailed May 13, 2009.
U.S. Appl. No. 12/167,852, Office Action mailed Feb. 29, 2012.
U.S. Appl. No. 12/167,852, Restriction Requirement mailed Jun. 3, 2011.
U.S. Appl. No. 12/771,511, Office Action mailed Mar. 4, 2012.
U.S. Appl. No. 12/771,511, Restriction Requirement mailed Dec. 21, 2011.
U.S. Appl. No. 60/693,988 entitled "Methods and Compositions for Modulating COX-2" by Michael P. Belmares et al., filed Jun. 23, 2005.
U.S. Appl. No. 60/775,315 entitled "Small Molecule Inhibitors of PDZ Interactions" by Michael P. Belmares et al., filed Dec. 30, 2005.
Weggen et al., "A subset of NSAIDs lower amyloidogenic A-beta-42 independently of cyclooxygenase activity", *Nature*, 414:212-216, (2001).
"Rote Liste 2002", Rote Liste Service GMBH, Frankfurt/Main, XP002433258, paragraph 05-330, 2002.
Giuliani et al., "Synthesis, Biological Data and Correlation Analysis in a Set of Analgesic Drugs," Farmaco—Ed. Sc., 38:847-864, (1983).
International Search Report and Written Opinion mailed Jun. 12, 2007 for application PCT/US2006/062715.
Isnardi et al., "Different Effects of the Treatment with AGN 193836 and 9-Cis Retinoic Acid in Breast Cancer Cells," AntiCancer Research, 19:3083-3092, (1999).
Sota et al., "Antiinflammatory Activities of Related Compounds to Anthranilic Acid. I. On N-Phenylanthranilic Acid Derivatives," Yakugaku Zasshi (Pharmaceutical Society of Japan), 89(10):1392-1400, (1969).
European Patent Application No. 06846858.6 (now Patent No. EP1976502), Office Action mailed Jun. 4, 2009.
International Search Report mailed for application PCT/US2003/036698 (WO2004/045535A3).
Kidd et al, "Mechanisms of inflammatory pain,"British Journal of Anesthesia, 87(1):3-11,(2001).
U.S. Appl. No. 12/771,511, Non-Final Office Action mailed Jun. 5, 2013.
Woolf, "Pain: Moving from Symptom Control toward Mechanism-Specific Pharmacologic Management,"Am. Intern. Med., 140:441-451, (2004).

\* cited by examiner

Competition of PDZ/PL Interactions by Small Molecule Compounds:
y-axis: $OD_{450}$ nm values Small Molecule Inhibitors of PDZ/PL Interactions Small Molecule Inhibitors of PDZ/PL Interactions

Titration Analysis of Small Molecule Competitors
Having Apparent IC50 values < 250 µM

Panel 1) Titrations for Compound #3289-2331

Panel 2) Titrations for Compound # 0620-0057

Panel 3) Titrations for Compound #C450-0454

Panel 4) Titrations for Compound #3558-0042

Panel 5) Titrations for Compound # MC 247808

Panel 6) Titrations for Compound # E544-0129

Small Molecule-Peptide Chimeric Conjugates

Small Molecule-Peptide Chimeric Conjugates

PSD-95 Level Reduction In the Presence of Compound 0620-0057

Biotin-YGRKKRRQRRRKLSSIESDV (Biotin-TATNR2B9c)
Ac-RQIKIWFQNRRMKWKKKLSSIESDV (Antennapedia-NR2B9c)

SEQUENCE LISTING

```
<160> NUMBER OF SEQ ID NOS: 90

<210> SEQ ID NO 1
<211> LENGTH: 20
<212> TYPE: PRT
<213> ORGANISM: Artificial
<220> FEATURE:
<223> OTHER INFORMATION: Synthetic PL peptide 1857

<400> SEQUENCE: 1

Gly Arg Trp Thr Gly Arg Ser Met Ser Ser Trp Lys Pro Thr Arg Arg
1               5                   10                  15

Glu Thr Glu Val
            20

<210> SEQ ID NO 2
<211> LENGTH: 20
<212> TYPE: PRT
<213> ORGANISM: Artificial
<220> FEATURE:
<223> OTHER INFORMATION: Synthetic PL peptide AA56

<400> SEQUENCE: 2

Gln Ile Ser Pro Gly Gly Leu Glu Pro Pro Ser Glu Lys His Phe Arg
1               5                   10                  15

Glu Thr Glu Val
            20

<210> SEQ ID NO 3
<211> LENGTH: 20
<212> TYPE: PRT
<213> ORGANISM: Artificial
<220> FEATURE:
<223> OTHER INFORMATION: Synthetic PL peptide 1965

<400> SEQUENCE: 3

Tyr Gly Arg Lys Lys Arg Arg Gln Arg Arg Tyr Ile Pro Glu Ala
1               5                   10                  15

Gln Thr Arg Leu
            20

<210> SEQ ID NO 4
```

```
<211> LENGTH: 20
<212> TYPE: PRT
<213> ORGANISM: Artificial
<220> FEATURE:
<223> OTHER INFORMATION: Synthetic PL peptide 1916

<400> SEQUENCE: 4

Tyr Gly Arg Lys Lys Arg Arg Gln Arg Arg Thr Lys Asn Tyr Lys
1               5                   10                  15

Gln Thr Ser Val
            20

<210> SEQ ID NO 5
<211> LENGTH: 11
<212> TYPE: PRT
<213> ORGANISM: Artificial
<220> FEATURE:
<223> OTHER INFORMATION: Synthetic tat internalization peptide

<400> SEQUENCE: 5

Tyr Gly Arg Lys Lys Arg Arg Gln Arg Arg Arg
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic internalization peptide
<220> FEATURE:
<221> NAME/KEY: MISC_FEATURE
<222> LOCATION: (1)..(1)
<223> OTHER INFORMATION: Xaa is an amino acid other than Tyr or absent

<400> SEQUENCE: 6

Xaa Gly Arg Lys Lys Arg Arg Gln Arg Arg Arg
1               5                   10

<210> SEQ ID NO 7
<211> LENGTH: 11
<212> TYPE: PRT
<213> ORGANISM: Artificial
<220> FEATURE:
<223> OTHER INFORMATION: Synthetic tat variant internalization peptide

<400> SEQUENCE: 7

Phe Gly Arg Lys Lys Arg Arg Gln Arg Arg Arg
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic tat variant internalization peptide

<400> SEQUENCE: 8

Gly Arg Lys Lys Arg Arg Gln Arg Arg Arg
1               5                   10

<210> SEQ ID NO 9
<211> LENGTH: 5
<212> TYPE: PRT
<213> ORGANISM: Artificial
<220> FEATURE:
<223> OTHER INFORMATION: Synthetic peptide

<400> SEQUENCE: 9
```

```
Gly Ser Ser Ser Ser
1               5

<210> SEQ ID NO 10
<211> LENGTH: 5
<212> TYPE: PRT
<213> ORGANISM: Artificial
<220> FEATURE:
<223> OTHER INFORMATION: Synthetic peptide

<400> SEQUENCE: 10

Thr Gly Glu Lys Pro
1               5

<210> SEQ ID NO 11
<211> LENGTH: 8
<212> TYPE: PRT
<213> ORGANISM: Artificial
<220> FEATURE:
<223> OTHER INFORMATION: Synthetic peptide

<400> SEQUENCE: 11

Gly Gly Arg Arg Gly Gly Gly Ser
1               5

<210> SEQ ID NO 12
<211> LENGTH: 9
<212> TYPE: PRT
<213> ORGANISM: Artificial
<220> FEATURE:
<223> OTHER INFORMATION: Synthetic peptide

<400> SEQUENCE: 12

Leu Arg Gln Arg Asp Gly Glu Arg Pro
1               5

<210> SEQ ID NO 13
<211> LENGTH: 20
<212> TYPE: PRT
<213> ORGANISM: Artificial
<220> FEATURE:
<223> OTHER INFORMATION: Synthetic peptide

<400> SEQUENCE: 13

Phe Gly Arg Lys Lys Arg Arg Gln Arg Arg Lys Leu Ser Ser Ile
1               5                   10                  15

Glu Ser Asp Val
            20

<210> SEQ ID NO 14
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Phe modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 14

Xaa Gly Arg Lys Lys Arg Arg Gln Arg Arg Lys Leu Ser Ser Ile
1               5                   10                  15

Glu Ser Asp Val
            20
```

```
<210> SEQ ID NO 15
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 15

Xaa Phe Gly Arg Lys Lys Arg Arg Gln Arg Arg Arg Lys Leu Ser Ser
1               5                   10                  15

Ile Glu Ser Asp Val
            20

<210> SEQ ID NO 16
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 16

Xaa Phe Gly Arg Lys Lys Arg Arg Gln Arg Arg Arg Lys Leu Ser Ser
1               5                   10                  15

Ile Glu Ser Asp Val
            20

<210> SEQ ID NO 17
<211> LENGTH: 19
<212> TYPE: PRT
<213> ORGANISM: Artificial
<220> FEATURE:
<223> OTHER INFORMATION: Synthetic peptide

<400> SEQUENCE: 17

Gly Lys Lys Lys Lys Lys Gln Lys Lys Lys Lys Leu Ser Ser Ile Glu
1               5                   10                  15

Ser Asp Val

<210> SEQ ID NO 18
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 18

Xaa Lys Lys Lys Lys Lys Gln Lys Lys Lys Lys Leu Ser Ser Ile Glu
1               5                   10                  15

Ser Asp Val

<210> SEQ ID NO 19
```

```
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 19

Xaa Gly Lys Lys Lys Lys Lys Gln Lys Lys Lys Lys Leu Ser Ser Ile
1               5                   10                  15

Glu Ser Asp Val
            20

<210> SEQ ID NO 20
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 20

Xaa Gly Lys Lys Lys Lys Lys Gln Lys Lys Lys Lys Leu Ser Ser Ile
1               5                   10                  15

Glu Ser Asp Val
            20

<210> SEQ ID NO 21
<211> LENGTH: 18
<212> TYPE: PRT
<213> ORGANISM: Artificial
<220> FEATURE:
<223> OTHER INFORMATION: Synthetic peptide

<400> SEQUENCE: 21

Arg Lys Lys Arg Arg Gln Arg Arg Lys Leu Ser Ser Ile Glu Ser
1               5                   10                  15

Asp Val

<210> SEQ ID NO 22
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 22

Xaa Lys Lys Arg Arg Gln Arg Arg Lys Leu Ser Ser Ile Glu Ser
1               5                   10                  15

Asp Val

<210> SEQ ID NO 23
<211> LENGTH: 19
<212> TYPE: PRT
<213> ORGANISM: Artificial
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 23

Xaa Arg Lys Lys Arg Arg Gln Arg Arg Arg Lys Leu Ser Ser Ile Glu
1               5                   10                  15

Ser Asp Val

<210> SEQ ID NO 24
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 24

Xaa Arg Lys Lys Arg Arg Gln Arg Arg Arg Lys Leu Ser Ser Ile Glu
1               5                   10                  15

Ser Asp Val

<210> SEQ ID NO 25
<211> LENGTH: 19
<212> TYPE: PRT
<213> ORGANISM: Artificial
<220> FEATURE:
<223> OTHER INFORMATION: Synthetic peptide

<400> SEQUENCE: 25

Gly Ala Lys Lys Arg Arg Gln Arg Arg Arg Lys Leu Ser Ser Ile Glu
1               5                   10                  15

Ser Asp Val

<210> SEQ ID NO 26
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 26

Xaa Ala Lys Lys Arg Arg Gln Arg Arg Arg Lys Leu Ser Ser Ile Glu
1               5                   10                  15

Ser Asp Val

<210> SEQ ID NO 27
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
```

<223> OTHER INFORMATION: Xaa is pyroglutamate

<400> SEQUENCE: 27

Xaa Gly Ala Lys Lys Arg Arg Gln Arg Arg Arg Lys Leu Ser Ser Ile
1               5                   10                  15

Glu Ser Asp Val
            20

<210> SEQ ID NO 28
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 28

Xaa Gly Ala Lys Lys Arg Arg Gln Arg Arg Arg Lys Leu Ser Ser Ile
1               5                   10                  15

Glu Ser Asp Val
            20

<210> SEQ ID NO 29
<211> LENGTH: 18
<212> TYPE: PRT
<213> ORGANISM: Artificial
<220> FEATURE:
<223> OTHER INFORMATION: Synthetic peptide

<400> SEQUENCE: 29

Ala Lys Lys Arg Arg Gln Arg Arg Arg Lys Leu Ser Ser Ile Glu Ser
1               5                   10                  15

Asp Val

<210> SEQ ID NO 30
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Ala modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 30

Xaa Lys Lys Arg Arg Gln Arg Arg Arg Lys Leu Ser Ser Ile Glu Ser
1               5                   10                  15

Asp Val

<210> SEQ ID NO 31
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 31

```
Xaa Ala Lys Lys Arg Arg Gln Arg Arg Arg Lys Leu Ser Ser Ile Glu
1               5                   10                  15

Ser Asp Val

<210> SEQ ID NO 32
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 32

Xaa Ala Lys Lys Arg Arg Gln Arg Arg Arg Lys Leu Ser Ser Ile Glu
1               5                   10                  15

Ser Asp Val

<210> SEQ ID NO 33
<211> LENGTH: 19
<212> TYPE: PRT
<213> ORGANISM: Artificial
<220> FEATURE:
<223> OTHER INFORMATION: Synthetic peptide

<400> SEQUENCE: 33

Gly Arg Lys Ala Arg Arg Gln Arg Arg Arg Lys Leu Ser Ser Ile Glu
1               5                   10                  15

Ser Asp Val

<210> SEQ ID NO 34
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 34

Xaa Arg Lys Ala Arg Arg Gln Arg Arg Arg Lys Leu Ser Ser Ile Glu
1               5                   10                  15

Ser Asp Val

<210> SEQ ID NO 35
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 35

Xaa Gly Arg Lys Ala Arg Arg Gln Arg Arg Arg Lys Leu Ser Ser Ile
1               5                   10                  15

Glu Ser Asp Val
```

-continued

```
<210> SEQ ID NO 36
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 36

Xaa Gly Arg Lys Ala Arg Arg Gln Arg Arg Lys Leu Ser Ser Ile
1               5                   10                  15

Glu Ser Asp Val
            20

<210> SEQ ID NO 37
<211> LENGTH: 18
<212> TYPE: PRT
<213> ORGANISM: Artificial
<220> FEATURE:
<223> OTHER INFORMATION: Synthetic peptide

<400> SEQUENCE: 37

Arg Lys Ala Arg Arg Gln Arg Arg Lys Leu Ser Ser Ile Glu Ser
1               5                   10                  15

Asp Val

<210> SEQ ID NO 38
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 38

Xaa Lys Ala Arg Arg Gln Arg Arg Lys Leu Ser Ser Ile Glu Ser
1               5                   10                  15

Asp Val

<210> SEQ ID NO 39
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 39

Xaa Arg Lys Ala Arg Arg Gln Arg Arg Lys Leu Ser Ser Ile Glu
1               5                   10                  15

Ser Asp Val

<210> SEQ ID NO 40
```

```
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 40

Xaa Arg Lys Ala Arg Gln Arg Arg Arg Lys Leu Ser Ser Ile Glu
1               5                   10                  15

Ser Asp Val

<210> SEQ ID NO 41
<211> LENGTH: 19
<212> TYPE: PRT
<213> ORGANISM: Artificial
<220> FEATURE:
<223> OTHER INFORMATION: Synthetic peptide

<400> SEQUENCE: 41

Gly Arg Lys Lys Ala Arg Gln Arg Arg Arg Lys Leu Ser Ser Ile Glu
1               5                   10                  15

Ser Asp Val

<210> SEQ ID NO 42
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 42

Xaa Arg Lys Lys Ala Arg Gln Arg Arg Arg Lys Leu Ser Ser Ile Glu
1               5                   10                  15

Ser Asp Val

<210> SEQ ID NO 43
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 43

Xaa Gly Arg Lys Lys Ala Arg Gln Arg Arg Arg Lys Leu Ser Ser Ile
1               5                   10                  15

Glu Ser Asp Val
            20

<210> SEQ ID NO 44
<211> LENGTH: 20
<212> TYPE: PRT
<213> ORGANISM: Artificial
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 44

Xaa Gly Arg Lys Lys Ala Arg Gln Arg Arg Lys Leu Ser Ser Ile
1               5                   10                  15

Glu Ser Asp Val
            20

<210> SEQ ID NO 45
<211> LENGTH: 18
<212> TYPE: PRT
<213> ORGANISM: Artificial
<220> FEATURE:
<223> OTHER INFORMATION: Synthetic peptide

<400> SEQUENCE: 45

Arg Lys Lys Ala Arg Gln Arg Arg Lys Leu Ser Ser Ile Glu Ser
1               5                   10                  15

Asp Val

<210> SEQ ID NO 46
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 46

Xaa Lys Lys Ala Arg Gln Arg Arg Lys Leu Ser Ser Ile Glu Ser
1               5                   10                  15

Asp Val

<210> SEQ ID NO 47
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 47

Xaa Arg Lys Lys Ala Arg Gln Arg Arg Arg Lys Leu Ser Ser Ile Glu
1               5                   10                  15

Ser Asp Val

<210> SEQ ID NO 48
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
```

<223> OTHER INFORMATION: Xaa is an amino acid other than Tyr

<400> SEQUENCE: 48

Xaa Arg Lys Lys Ala Arg Gln Arg Arg Arg Lys Leu Ser Ser Ile Glu
1               5                   10                  15

Ser Asp Val

<210> SEQ ID NO 49
<211> LENGTH: 19
<212> TYPE: PRT
<213> ORGANISM: Artificial
<220> FEATURE:
<223> OTHER INFORMATION: Synthetic peptide

<400> SEQUENCE: 49

Gly Arg Lys Lys Arg Arg Gln Ala Arg Arg Lys Leu Ser Ser Ile Glu
1               5                   10                  15

Ser Asp Val

<210> SEQ ID NO 50
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 50

Xaa Arg Lys Lys Arg Arg Gln Ala Arg Arg Lys Leu Ser Ser Ile Glu
1               5                   10                  15

Ser Asp Val

<210> SEQ ID NO 51
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 51

Xaa Gly Arg Lys Lys Arg Arg Gln Ala Arg Arg Lys Leu Ser Ser Ile
1               5                   10                  15

Glu Ser Asp Val
            20

<210> SEQ ID NO 52
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 52

-continued

```
Xaa Gly Arg Lys Lys Arg Arg Gln Ala Arg Arg Lys Leu Ser Ser Ile
1               5                   10                  15

Glu Ser Asp Val
            20

<210> SEQ ID NO 53
<211> LENGTH: 18
<212> TYPE: PRT
<213> ORGANISM: Artificial
<220> FEATURE:
<223> OTHER INFORMATION: Synthetic peptide

<400> SEQUENCE: 53

Arg Lys Lys Arg Arg Gln Ala Arg Arg Lys Leu Ser Ser Ile Glu Ser
1               5                   10                  15

Asp Val

<210> SEQ ID NO 54
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 54

Xaa Lys Lys Arg Arg Gln Ala Arg Arg Lys Leu Ser Ser Ile Glu Ser
1               5                   10                  15

Asp Val

<210> SEQ ID NO 55
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 55

Xaa Arg Lys Lys Arg Arg Gln Ala Arg Arg Lys Leu Ser Ser Ile Glu
1               5                   10                  15

Ser Asp Val

<210> SEQ ID NO 56
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 56

Xaa Arg Lys Lys Arg Arg Gln Ala Arg Arg Lys Leu Ser Ser Ile Glu
1               5                   10                  15

Ser Asp Val
```

<210> SEQ ID NO 57
<211> LENGTH: 19
<212> TYPE: PRT
<213> ORGANISM: Artificial
<220> FEATURE:
<223> OTHER INFORMATION: Synthetic peptide

<400> SEQUENCE: 57

Gly Arg Lys Lys Arg Arg Gln Arg Ala Arg Lys Leu Ser Ser Ile Glu
1               5                   10                  15

Ser Asp Val

<210> SEQ ID NO 58
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 58

Xaa Arg Lys Lys Arg Arg Gln Arg Ala Arg Lys Leu Ser Ser Ile Glu
1               5                   10                  15

Ser Asp Val

<210> SEQ ID NO 59
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 59

Xaa Gly Arg Lys Lys Arg Arg Gln Arg Ala Arg Lys Leu Ser Ser Ile
1               5                   10                  15

Glu Ser Asp Val
            20

<210> SEQ ID NO 60
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 60

Xaa Gly Arg Lys Lys Arg Arg Gln Arg Ala Arg Lys Leu Ser Ser Ile
1               5                   10                  15

Glu Ser Asp Val
            20

<210> SEQ ID NO 61

```
<211> LENGTH: 18
<212> TYPE: PRT
<213> ORGANISM: Artificial
<220> FEATURE:
<223> OTHER INFORMATION: Synthetic peptide

<400> SEQUENCE: 61

Arg Lys Lys Arg Arg Gln Arg Ala Arg Lys Leu Ser Ser Ile Glu Ser
1               5                   10                  15

Asp Val

<210> SEQ ID NO 62
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 62

Xaa Lys Lys Arg Arg Gln Arg Ala Arg Lys Leu Ser Ser Ile Glu Ser
1               5                   10                  15

Asp Val

<210> SEQ ID NO 63
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 63

Xaa Arg Lys Lys Arg Arg Gln Arg Ala Arg Lys Leu Ser Ser Ile Glu
1               5                   10                  15

Ser Asp Val

<210> SEQ ID NO 64
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 64

Xaa Arg Lys Lys Arg Arg Gln Arg Ala Arg Lys Leu Ser Ser Ile Glu
1               5                   10                  15

Ser Asp Val

<210> SEQ ID NO 65
<211> LENGTH: 20
<212> TYPE: PRT
<213> ORGANISM: Artificial
<220> FEATURE:
<223> OTHER INFORMATION: Synthetic peptide
```

<400> SEQUENCE: 65

Arg Arg Pro Arg Arg Pro Arg Arg Pro Arg Arg Lys Leu Ser Ser Ile
1               5                   10                  15

Glu Ser Asp Val
            20

<210> SEQ ID NO 66
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 66

Xaa Arg Pro Arg Arg Pro Arg Arg Pro Arg Arg Lys Leu Ser Ser Ile
1               5                   10                  15

Glu Ser Asp Val
            20

<210> SEQ ID NO 67
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 67

Xaa Arg Arg Pro Arg Arg Pro Arg Arg Pro Arg Arg Lys Leu Ser Ser
1               5                   10                  15

Ile Glu Ser Asp Val
            20

<210> SEQ ID NO 68
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 68

Xaa Arg Arg Pro Arg Arg Pro Arg Arg Pro Arg Arg Lys Leu Ser Ser
1               5                   10                  15

Ile Glu Ser Asp Val
            20

<210> SEQ ID NO 69
<211> LENGTH: 20
<212> TYPE: PRT
<213> ORGANISM: Artificial
<220> FEATURE:
<223> OTHER INFORMATION: Synthetic peptide

```
<400> SEQUENCE: 69

Arg Arg Ala Arg Arg Ala Arg Arg Ala Arg Arg Lys Leu Ser Ser Ile
1               5                   10                  15

Glu Ser Asp Val
            20

<210> SEQ ID NO 70
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 70

Xaa Arg Ala Arg Arg Ala Arg Arg Ala Arg Arg Lys Leu Ser Ser Ile
1               5                   10                  15

Glu Ser Asp Val
            20

<210> SEQ ID NO 71
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 71

Xaa Arg Arg Ala Arg Arg Ala Arg Arg Ala Arg Arg Lys Leu Ser Ser
1               5                   10                  15

Ile Glu Ser Asp Val
            20

<210> SEQ ID NO 72
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 72

Xaa Arg Arg Ala Arg Arg Ala Arg Arg Ala Arg Arg Lys Leu Ser Ser
1               5                   10                  15

Ile Glu Ser Asp Val
            20

<210> SEQ ID NO 73
<211> LENGTH: 19
<212> TYPE: PRT
<213> ORGANISM: Artificial
<220> FEATURE:
<223> OTHER INFORMATION: Synthetic peptide

<400> SEQUENCE: 73
```

```
Arg Arg Arg Ala Arg Arg Arg Ala Arg Arg Lys Leu Ser Ser Ile Glu
1               5                   10                  15

Ser Asp Val

<210> SEQ ID NO 74
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 74

Xaa Arg Arg Ala Arg Arg Arg Ala Arg Arg Lys Leu Ser Ser Ile Glu
1               5                   10                  15

Ser Asp Val

<210> SEQ ID NO 75
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 75

Xaa Arg Arg Arg Ala Arg Arg Arg Ala Arg Arg Lys Leu Ser Ser Ile
1               5                   10                  15

Glu Ser Asp Val
            20

<210> SEQ ID NO 76
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 76

Xaa Arg Arg Arg Ala Arg Arg Arg Ala Arg Arg Lys Leu Ser Ser Ile
1               5                   10                  15

Glu Ser Asp Val
            20

<210> SEQ ID NO 77
<211> LENGTH: 19
<212> TYPE: PRT
<213> ORGANISM: Artificial
<220> FEATURE:
<223> OTHER INFORMATION: Synthetic peptide

<400> SEQUENCE: 77

Arg Arg Arg Pro Arg Arg Arg Pro Arg Arg Lys Leu Ser Ser Ile Glu
1               5                   10                  15
```

Ser Asp Val

<210> SEQ ID NO 78
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 78

Xaa Arg Arg Pro Arg Arg Arg Pro Arg Arg Lys Leu Ser Ser Ile Glu
1               5                   10                  15

Ser Asp Val

<210> SEQ ID NO 79
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 79

Xaa Arg Arg Arg Pro Arg Arg Arg Pro Arg Arg Lys Leu Ser Ser Ile
1               5                   10                  15

Glu Ser Asp Val
            20

<210> SEQ ID NO 80
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 80

Xaa Arg Arg Arg Pro Arg Arg Arg Pro Arg Arg Lys Leu Ser Ser Ile
1               5                   10                  15

Glu Ser Asp Val
            20

<210> SEQ ID NO 81
<211> LENGTH: 17
<212> TYPE: PRT
<213> ORGANISM: Artificial
<220> FEATURE:
<223> OTHER INFORMATION: Synthetic peptide

<400> SEQUENCE: 81

Arg Arg Pro Arg Arg Pro Arg Arg Lys Leu Ser Ser Ile Glu Ser Asp
1               5                   10                  15

Val

<210> SEQ ID NO 82
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 82

Xaa Arg Pro Arg Arg Pro Arg Arg Lys Leu Ser Ser Ile Glu Ser Asp
1               5                   10                  15

Val

<210> SEQ ID NO 83
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 83

Xaa Arg Arg Pro Arg Arg Pro Arg Arg Lys Leu Ser Ser Ile Glu Ser
1               5                   10                  15

Asp Val

<210> SEQ ID NO 84
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 84

Xaa Arg Arg Pro Arg Arg Pro Arg Arg Lys Leu Ser Ser Ile Glu Ser
1               5                   10                  15

Asp Val

<210> SEQ ID NO 85
<211> LENGTH: 17
<212> TYPE: PRT
<213> ORGANISM: Artificial
<220> FEATURE:
<223> OTHER INFORMATION: Synthetic peptide

<400> SEQUENCE: 85

Arg Arg Ala Arg Arg Ala Arg Arg Lys Leu Ser Ser Ile Glu Ser Asp
1               5                   10                  15

Val

<210> SEQ ID NO 86
<211> LENGTH: 17
<212> TYPE: PRT
<213> ORGANISM: Artificial

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 86

Xaa Arg Ala Arg Arg Ala Arg Arg Lys Leu Ser Ser Ile Glu Ser Asp
1               5                   10                  15

Val

<210> SEQ ID NO 87
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 87

Xaa Arg Arg Ala Arg Arg Ala Arg Arg Lys Leu Ser Ser Ile Glu Ser
1               5                   10                  15

Asp Val

<210> SEQ ID NO 88
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 88

Xaa Arg Arg Ala Arg Arg Ala Arg Arg Lys Leu Ser Ser Ile Glu Ser
1               5                   10                  15

Asp Val

<210> SEQ ID NO 89
<211> LENGTH: 25
<212> TYPE: PRT
<213> ORGANISM: Artificial
<220> FEATURE:
<223> OTHER INFORMATION: Synthetic peptide - Antennapedia-NR2B9c
<220> FEATURE:
<221> NAME/KEY: MOD_RES
<222> LOCATION: (1)..(1)
<223> OTHER INFORMATION: ACETYLATION

<400> SEQUENCE: 89

Arg Gln Ile Lys Ile Trp Phe Gln Asn Arg Arg Met Lys Trp Lys Lys
1               5                   10                  15

Lys Leu Ser Ser Ile Glu Ser Asp Val
            20                  25

<210> SEQ ID NO 90
<211> LENGTH: 20
<212> TYPE: PRT
<213> ORGANISM: Artificial
```

```
<220> FEATURE:
<223> OTHER INFORMATION: Synthetic peptide - Tat-NR2B9c

<400> SEQUENCE: 90

Tyr Gly Arg Lys Lys Arg Arg Gln Arg Arg Lys Leu Ser Ser Ile
1               5                   10                  15

Glu Ser Asp Val
            20
```

SMALL MOLECULE INHIBITORS OF PDZ INTERACTIONS

CROSS REFERENCE TO RELATED APPLICATION

The present application claims the benefit of U.S. Ser. No. 60/947,883 filed Jul. 3, 2007, incorporated by reference in its entirety for all purposes. This application is also a continuation-in-part of PCT/US06/062715 filed Dec. 29, 2006, which claims the benefit of U.S. Ser. No. 60/755,315 filed Dec. 30, 2005, all of which are incorporated by reference in their entirety.

REFERENCE TO A "SEQUENCE LISTING," A TABLE, OR A COMPUTER PROGRAM LISTING SUBMITTED IN COMPUTER READABLE FORMAT

The Sequence Listing written in file 026373000810US_SeqList.txt is 33,679 bytes, and was created on Jul. 3, 2008, for the application filed herewith, Belmares et al. "SMALL MOLECULE INHIBITORS OF PDZ INTERACTIONS." The information contained in this file is hereby incorporated by reference.

BACKGROUND OF THE INVENTION

This application is related to U.S. Provisional Application No. 60/755,315 filed Dec. 30, 2005 and to U.S. patent application Ser. No. 11/426,282 filed Jun. 23, 2006, which claims priority to U.S. Provisional Application No. 60/693,988 filed Jun. 23, 2005, each of which is incorporated by reference in its entirety. In addition, copending International Application No. PCT/US2006/062715, which was filed on 29 Dec., 2006, is incorporated by reference in its entirety.

FIELD OF THE INVENTION

The present invention relates to molecular chemical pharmacology, protein biochemistry, cell biology and pathology. More particular the invention relates to the identification of small molecule inhibitors of PDZ domain binding and their use in diagnostics and therapeutics.

RELATED ART

PDZ domains are known to be involved in the organization of protein complexes at the plasma membrane. Polarized epithelial cells are characterized by unique protein content at their apical and basal-lateral surfaces, as well as at membrane junctions. Each of the latter apical or basal domains has a particular composition, including protein complexes with distinct transmembrane, membrane-associated, and cytosolic components. These protein complexes mediate a wide variety of functions, including the adhesive properties of particular cells, the formation of the paracellular barrier, ion transport, and transmission of signals (growth, differentiation, and homeostasis) between adjacent cells.

Formation of these, and other, cellular macromolecular protein complexes are determined in large part by the interactions of modular protein-binding domains. These are structurally conserved interaction elements with unique molecular specificities that can be found within a variety of different proteins. Examples of these domains include SH3 domains, which recognize amino acid sequence variations around a basic Pro-X-X-Pro site; the SH2 and PTB domains, which recognize phosphotyrosine and contiguous residues; and PDZ domains. Because binding specificities are based on a few amino acid residues, these domains are uniquely suited to permit evolution of new protein interactions by coordinate mutations in the domain and target peptide sequence. These domains are, figuratively speaking, the glue that binds protein complexes together, and their unique specificity and regulated binding determine the distinct compositions of different functional complexes within cells.

The effects of interrupting interactions of PDZ proteins with their protein ligand (PL) binding partners offer the potential for the development of treatments for cancer, inflammation, and neurological disorders among others. The ability to screen and classify compounds for their effects on PDZ-ligand interactions is a valuable tool.

SUMMARY OF THE INVENTION

The present invention provides pharmaceutical compositions having the general structure of $P_0$-A-B-C-D-E, where D and E are optional, with the structures of these compounds described as follows. $P_0$ is:

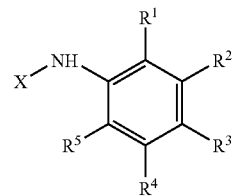

wherein one of $R^1$, $R^2$, $R^3$, $R^4$, and $R^5$ is —COOH, and wherein the remainder of $R^1$, $R^2$, $R^3$, $R^4$, and $R^5$ are selected from the group consisting of F, H, $OCH_3$ and $CH_3$; and X is -A-B-C-D-E, wherein A, B, C, D and E are connected through single bonds and A is selected from the group consisting of C=O, NH, $SO_2$ and $(CH_2)_m$, wherein m=0, 1, 2, 3, 4, or 5;

B is:

—$OCH_2$—, C=O,

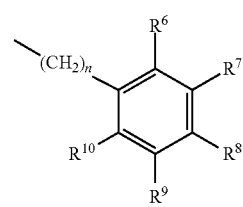

wherein one of $R^6$-$R^{10}$ is bonded to —C-D-E, and wherein the remainder of $R^6$-$R^{10}$ are selected from the group of H, OH, F, Cl, Br, I, $CH_3$, $CH_2CH_3$ and $OCH_3$, and n=0 or 1; or a ring system selected from the group consisting of saturated or unsaturated cycloalkyl or heterocycle; or

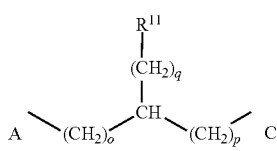

wherein o and p=0 or 1, q=0, 1, 2, 3 or 4, and $R^{11}$ is selected from the group consisting of substituted or unsubstituted lower alkyl, amide, thioether, phenyl, phenol, indole, imidazole, $NH(NH_2)(N(+)H_2)$, COOH, SH, OH, or H;

C is selected from the group consisting of —O—, C=O, NH, CONH, S, phthalamide, $CH_3$, H, $SO_2$ and $(CH_2)_r$, wherein r=0, 1, 2, 3, 4, or 5;

D is optional and when C is not terminating, D is selected from the group consisting of —CN—, C=O, NH, S, O, $SO_2$, $(CH_2)_s$, wherein s=0, 1, 2, 3, 4, or 5, and $(CH_2)_t$—OH, wherein t=0, 1, 2, 3, 4 or 5, and

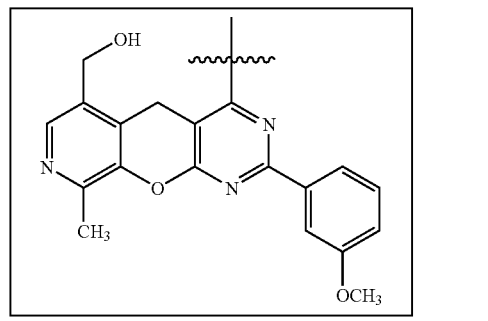

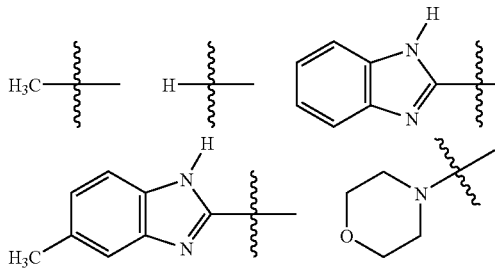

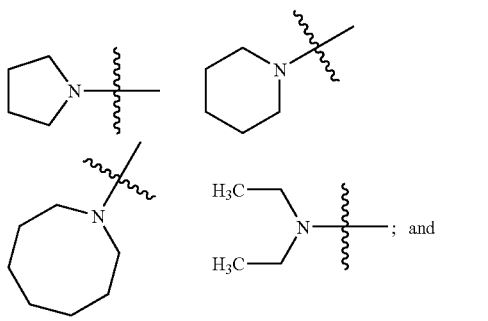

E is optional and when D is not terminating, E is cyclohexyl or phenyl, either substituted with lower alkyl, lower alkoxy, ketone, OH, COOH, nitroso, N-substituted indoline, or a cell membrane translocation peptide; or —$(CH_2)_u$—$(CHR^{12}R^{13})$, wherein u=0, 1, 2, 3, 4, 5, 6, 7, 8, 9, 10, 11, 12, 13, 14, 15, 16, or 17 and $R^{12}$ and $R^{13}$ are independently selected from the group consisting of H, OH, cyclohexane, cyclopentane, phenyl, substituted phenyl, cyclopentadiene; or branched lower alkyl including isopropyl, isobutyl, 1-isopropyl-2-methyl-butyl, 1-ethyl-propyl; or —NH—$COR^{14}$, wherein $R^{14}$ is $(CR^{15}R^{16})_vH$, wherein v=0, 1, 2, 3, 4, 5, 6, 7, 8, 9, 10, 11, 12, 13, 14, 15, 16, or 17 and $R^{15}$ and $R^{16}$ independently selected from the group consisting of H, cyclohexane, phenyl, and a cell membrane translocation peptide.

Alternatively, $P_0$ is:

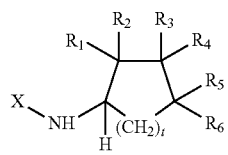

wherein t=0, 1 or 2, either $R^1$, $R^2$, $R^3$, $R^4$, $R^5$ or $R^6$ are COOH, and the remainder of $R^1$, $R^2$, $R^3$, $R^4$, $R^5$ and $R^6$ are selected from the group consisting of H, $CH_3$, F, and $OCH_3$, and X is -A-B-C-D-E, wherein A, B, C, D and E are connected through single bonds and A is selected from the group consisting of C=O, $SO_2$, NH, and $(CH_2)_m$, wherein m=0, 1, 2, 3, 4, or 5;

B is:

—$OCH_2$—, C=O; or

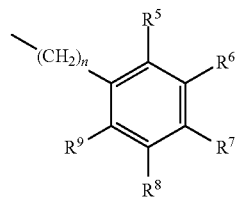

wherein one of $R^5$-$R^9$ is bonded to —C-D-E, and wherein the remainder of $R^5$-$R^9$ are selected from the group of H, OH, F, Cl, Br, I, $CH_3$, $CH_2CH_3$ and $OCH_3$, and n=0 or 1; or a ring system selected from the group consisting of saturated or unsaturated cycloalkyl or heterocycle; or

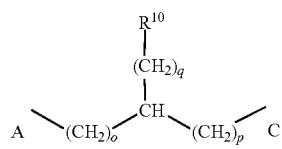

wherein o and p=0 or 1, and $R^{10}$ is selected from the group consisting of substituted or unsubstituted alkyl, amide, thioether, phenyl, phenol, indole, imidazole, $NH(NH_2)(N(+)H_2)$, COOH, SH, OH, or H;

C is selected from the group consisting of C=O, NH, S, phthalamide, —O—, $CH_3$, H, $SO_2$, and $(CH_2)_r$, wherein r=0, 1, 2, 3, 4, or 5;

D is optional and when C is not terminating, D is selected from the group consisting of C=O, —CN—, NH, S, O, $SO_2$, $(CH_2)_s$, wherein s=0, 1, 2, 3, 4, or 5, and

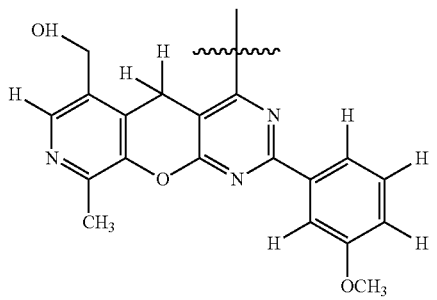

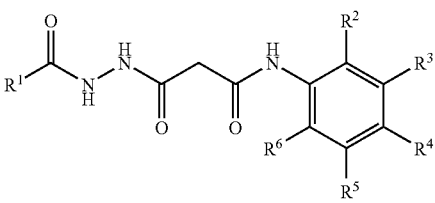

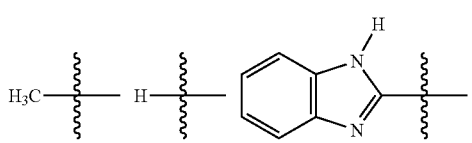

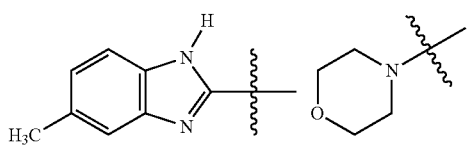

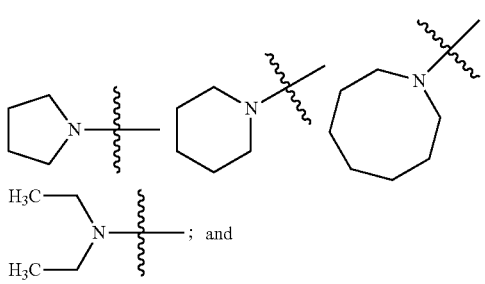

E is phenyl or cyclohexyl, either substituted with lower alkyl, lower alkoxy, ketone, OH, COOH, nitroso, N-substituted indoline; or —(CHR$^{11}$R$^{12}$)$_u$, wherein u=0, 1, 2, 3, 4, 5, 6, 7, 8, 9, 10, 11, 12, 13, 14, 15, 16, or 17 and R$^{11}$ and R$^{12}$ are independently selected from the group consisting of H, OH, cyclohexane, cyclopentane, phenyl, substituted phenyl, cyclopentadiene; or branched lower alkyl including isopropyl, isobutyl, 1-isopropyl-2-methyl-butyl, 1-ethyl-propyl; or —NH—COR$^{11}$, wherein R$^{11}$ is (CHR$^{12}$R$^{13}$)$_s$, wherein s=0, 1, 2, 3, 4, 5, 6, 7, 8, 9, 10, 11, 12, 13, 14, 15, 16, or 17 and R$^{12}$ and R$^{13}$ independently selected from the group consisting of H, cyclohexane, phenyl, and a cell membrane translocation peptide.

In certain embodiments, the present invention also provides methods of treating an adverse effect of a disease mediated by excitotoxicity, the method comprising administering to a subject in need thereof, an effective amount of a pharmaceutical compound of the invention. In some embodiments, the pharmaceutical compound of the invention has one of the structures depicted herein. In some embodiments, the compound has the following structure:

wherein R$^1$ is a member selected from the group consisting of cyclohexyl substituted with 0-4 R$^7$, phenyl substituted with 0-4 R$^7$, —(CH$_2$)$_u$—(CHR$^8$R$^9$), a branched C$_{1-6}$ alkyl (isopropyl, isobutyl, 1-isopropyl-2-methyl-butyl, 1-ethyl-propyl), and —NH—C(O)—(CR$^{10}$R$^{11}$)$_v$H;

each R$^7$ is independently a member selected from the group consisting of C$_{1-6}$ alkyl, C$_{1-6}$ alkoxy, —C(O)R$^{12}$, OH, COOH, —NO, N-substituted indoline and a cell membrane translocation peptide each R$^8$ and R$^9$ is independently selected from the group consisting of H, OH, cyclohexane, cyclopentane, phenyl, substituted phenyl (for instance, substituted with halo, alkyl and/or hydroxyl groups) and cyclopentadiene;

each R$^{10}$ and R$^{11}$ is independently selected from the group consisting of H, cyclohexane, phenyl and a cell membrane translocation peptide;

R$^{12}$ is a member selected from the group consisting of C$_{1-6}$ alkyl and aryl; and each of u and v are independently from 0 to 20;

wherein one of R$^2$, R$^3$, R$^4$, R$^5$ and R$^6$ is —COOH, and wherein the remainder of R$^2$, R$^3$, R$^4$, R$^5$ and R$^6$ are each independently selected from the group consisting of F, H, OCH$_3$ and CH$_3$.

Suitable compounds include compounds in which R1 is a P(O) residue depicted below, or R2 is an E residue depicted below, or compounds which contain any such R1 residue in combination with any such R2 residue. In another embodiment, R$^1$ is —(CH$_2$)$_u$—(CHR$^8$R$^9$). In yet another embodiment, R$^1$ is a member of the above-defined group of R1 substituents other than —(CH$_2$)$_u$—(CHR$^8$R$^9$).

The invention also provides pharmaceutical compositions including a compound having the following structure:

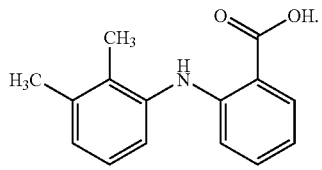 [SMILES: Cc1cccc(Nc2ccccc2C(=O)O)c1C]

Optionally, the administered compound is mixed with a pharmaceutical excipient as a pharmaceutical composition.

Non-limiting uses for compound of the present invention include the treatment of cancer, pain (e.g., chronic or acute), inflammation or neurological disorders, including clinical sequelae resulting therefrom. A compound of the present invention may be adminstered to illicit neuroprotective effects. In specific embodiments, the subject compounds may be administered to a subject suffering from pain and/or inflammation (e.g., arthritis, retinopathy, SLE, psoriasis, Bullous pemphigoid, shingles or a similar condition), a subject at risk of, or having undergone, microvascular insufficiency, hypoxia, stroke, atherosclerosis or another acute or chronic cardiovascular and neurological ischemic events patients with mild to severe traumatic brain injury, including diffuse axonal injury, hypoxic-ischemic encephalopathy and other forms of craniocerebral trauma, patients suffering from ischemic infarction, embolism and hemorrhage, e.g., hypotensive hemorrhage, subjects with neurodegenerative diseases including Alzheimer's disease, Lewy Body dementia, Parkinson's disease (PD), Huntington's disease (HD), multiple sclerosis, motor neuron disease, muscular dystrophy, peripheral neuropathies, metabolic disorders of the nervous system including glycogen storage diseases, and other conditions where neurons are damaged or destroyed, patients with abnormal immune activation, such as autoimmune SLE rheumatoid arthritis, Bullous pemphigoid, Type-I diabetes, and the like; while others may include those characterized by insufficient immune function. Other diseases that may be subject to treatment with compositions of the present invention include psychiatric disorders such as attention deficit hyperactive disorder, depression, agoraphobia, bulimia, anorexia, bipolar disorder, anxiety disorder, autism, dementia, dissociative disorder, hypochondriasis, impulse control disorder, kleptomania, mood disorder, multiple personality disorder, chronic fatigue syndrome, insomnia, narcolepsy, schizophrenia, substance abuse, post-traumatic stress disorder, obsessive-compulsive disorder, and manic depression. Compounds of the present invention can also be used to improve outcomes regarding addiction/addiction recovery. In certain embodiments, compounds of the present invention can modulate adrenergic receptor interactions, such as by, for example, disrupting these interactions. Compounds of the present invention can also be used to decrease (e.g., inhibit) cell proliferation.

The invention also provides methods of treating an adverse effect of a disease mediated by excitotoxicity comprising administering an effective amount of a compound to a subject, preferably a human, in need thereof. The compounds can be used for treatment of a patient having the disease, in which case the treatment reduces or inhibits further development of the adverse effect. Compounds used in such methods typically inhibits specific binding of PSD95 to NMDRA2B. Excitotoxic diseases treatable by the above methods include stroke, epilepsy, hypoxia, traumatic injury to the CNS not associated with stroke such as traumatic brain injury and spinal cord injury, Alzheimer's disease and Parkinson's disease.

In certain embodiments, the present invention contemplates a method of treating or reducing pain comprising administering an effective amount of a pharmaceutical composition to a subject in need thereof, wherein the pharmaceutical composition comprises any compound of the present invention. In particular embodiments, the pharmaceutical composition is further defined as

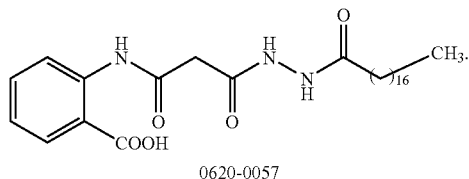

0620-0057

In certain embodiments, the present invention contemplates a method of treating a symptom associated with stroke comprising administering an effective amount of a pharmaceutical composition to a subject in need thereof, wherein the pharmaceutical composition comprises any compound of the present invention. In particular embodiments, the pharmaceutical composition is further defined as

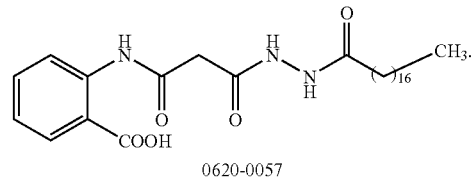

0620-0057

In other embodiments, the selected compound of the invention is any of the compounds or genera of compounds defined herein other than the compound 0620-0057 depicted above itself.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(9) Control: PL peptide 1857 (GRWTGRSMSSWKPTR-RETEV)+PDZ protein Magi1-d1;

(10) Test: PL peptide 1857 (GRWTGRSMSSWKPTR-RETEV)+PDZ protein Magi1-d1+compound 3019-0348;

(11) Control: PL peptide 1857 (GRWTGRSMSSWKPTR-RETEV)+PDZ protein Magi1-d1;

(12) Test: PL peptide 1857 (GRWTGRSMSSWKPTR-RETEV)+PDZ protein Magi1 d1+compound 3558-0042;

(13) Control: PL peptide 1857 (GRWTGRSMSSWKPTR-RETEV)+PDZ protein Magi1-d1;

(14) Test: PL peptide 1857 (GRWTGRSMSSWKPTR-RETEV)+PDZ protein Magi1-d1+compound MC 247808;

(15) Control: PL peptide 1916 (YGRKKRRQRRRT-KNYKQTSV)+PDZ protein PSD95-d3; and

(16) Test: PL peptide 1916 (YGRKKRRQRRRT-KNYKQTSV)+PDZ protein PSD95 d3+compound E544-0129.

As an example, the eight compounds in TABLE 1, (EXAMPLE 3, below), were identified in the small molecule screen: namely, 1) 8009-5039; 2) 3289-2331; 3) 0620-0057; 4) C450-0454; 5) 3019-0348; 6) 3558-0042; 7) MC 247808; and, 8) E544-0129.

Figure 1:
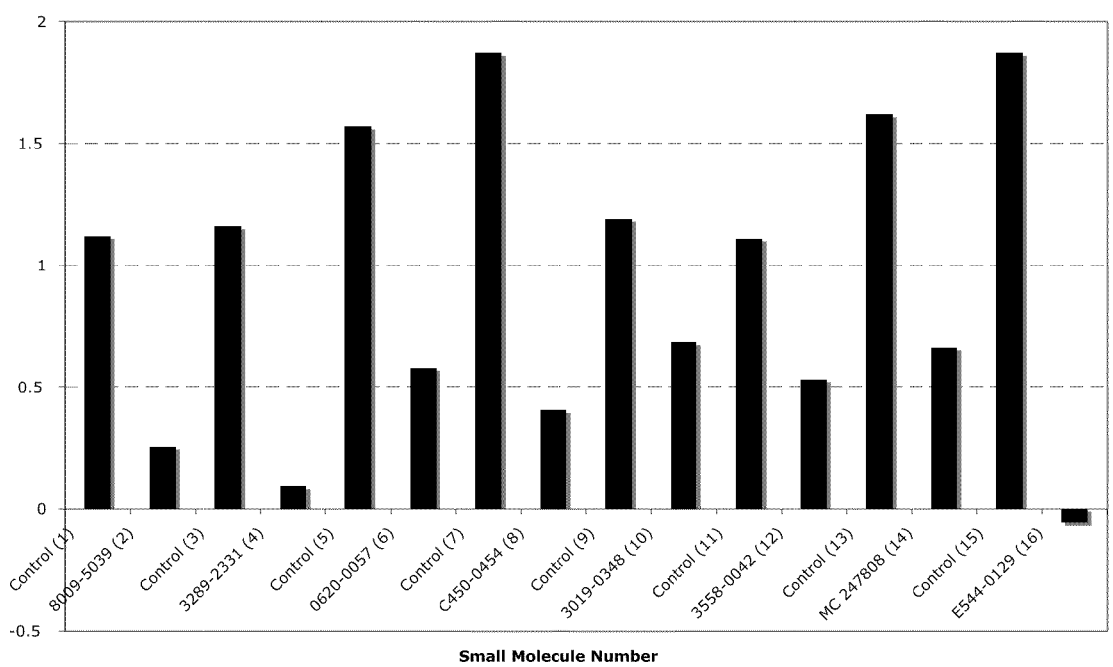
FIG. 1—Competition binding assays for identifying inhibitors of PDZ/PL interactions. The number in parenthesis refer to the PDZ/PL interaction and test compounds employed in the competition assays, as follows, namely:
(1) Control: PL peptide 1857 (GRWTGRSMSSWKPTR-RETEV)+PDZ protein Magi1 d1;
(2) Test: PL peptide 1857 (GRWTGRSMSSWKPTR-RETEV)+PDZ protein Magi1 d1+compound 8009-5039;
(3) Control: PL peptide AA56 (QISPGGLEPPSEKH-FRETEV)+PDZ protein Tip 1;
(4) Test: PL peptide AA56 (QISPGGLEPPSEKH-FRETEV)+PDZ protein Tip 1+compound 3289-2331;
(5) Control: PL peptide 1965 (YGRKKRRQRRRYI-PEAQTRL)+Shank 1;
(6) Test: PL peptide 1965 (YGRKKRRQRRRYI-PEAQTRL)+Shank 1+competitor 0620-005;
(7) Control: PL peptide 1916 (YGRKKRRQRRRT-KNYKQTSV)+PDZ protein PSD95-d3;
(8) Test: PL peptide 1916 (YGRKKRRQRRRT-KNYKQTSV)+PDZ protein PSD95-d3+compound C450-0454.
Figure 2A:
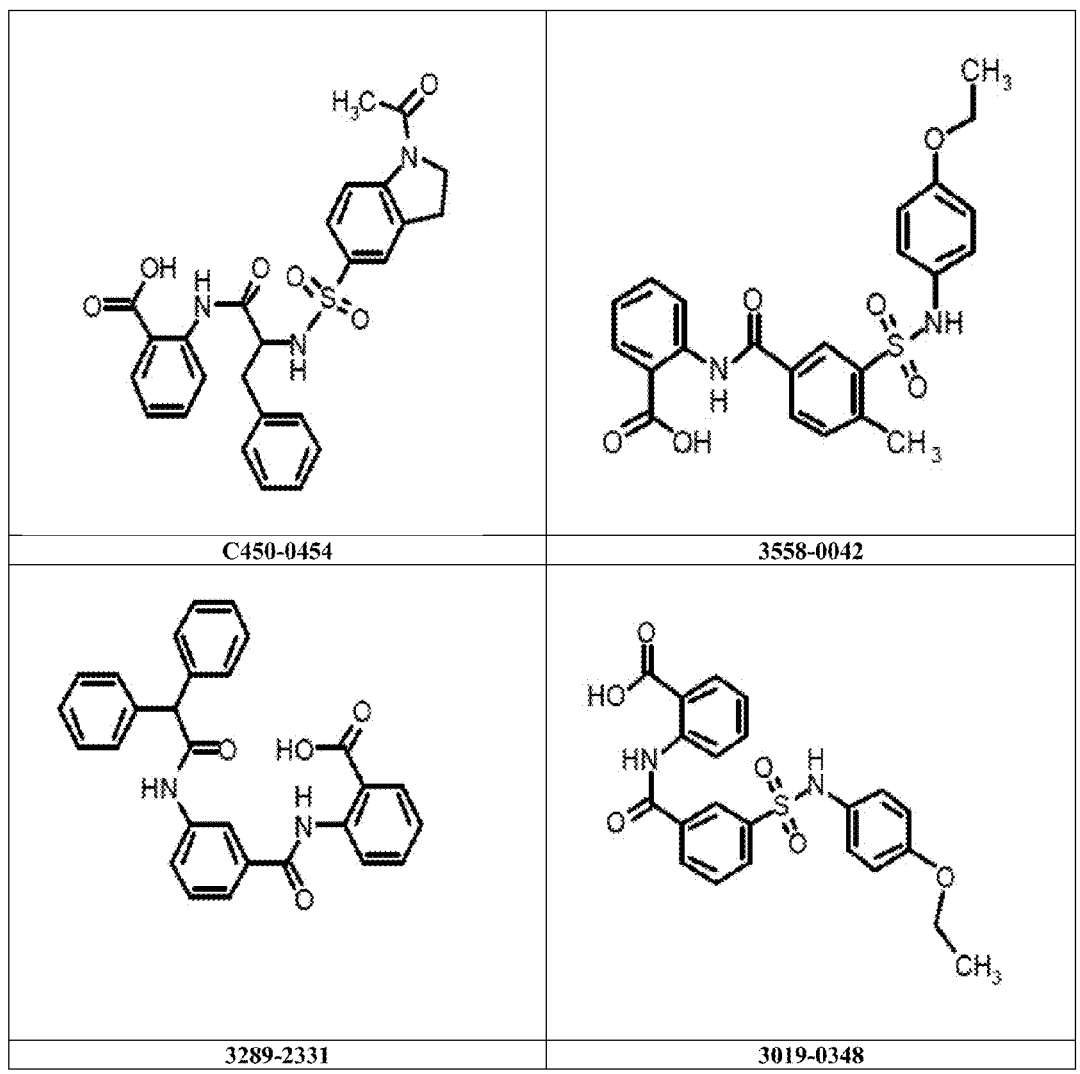
Figure 2A:
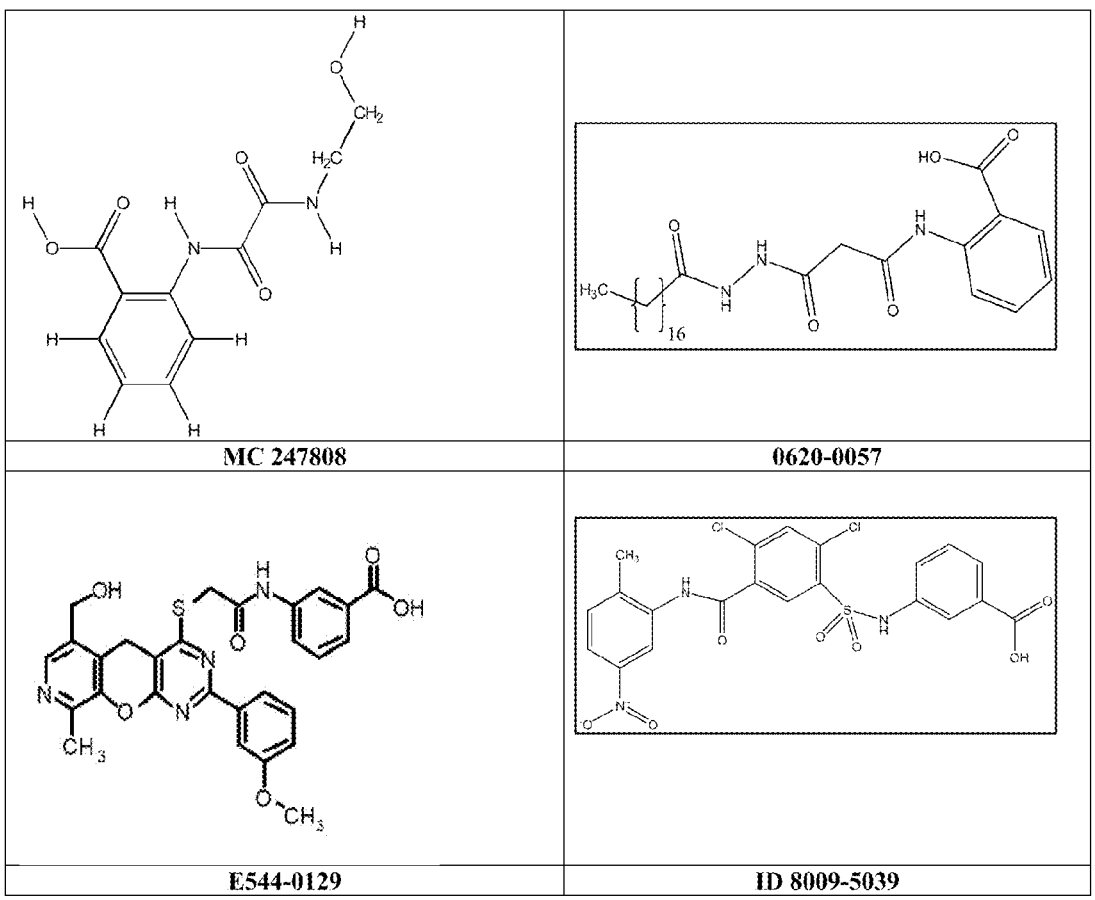
Figure 2B:
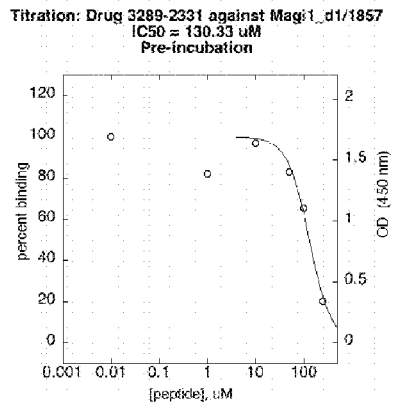
Figure 2B:
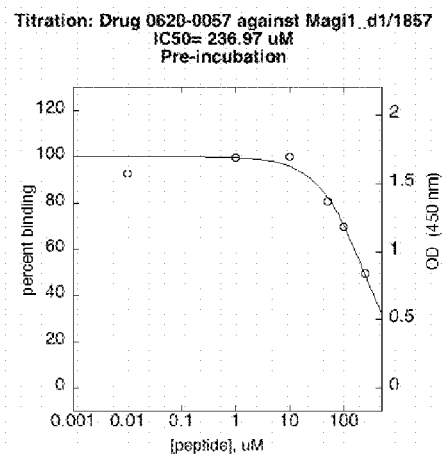
Figure 2B:
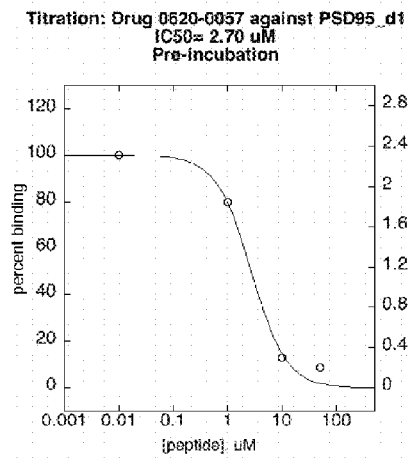
Figure 2B:
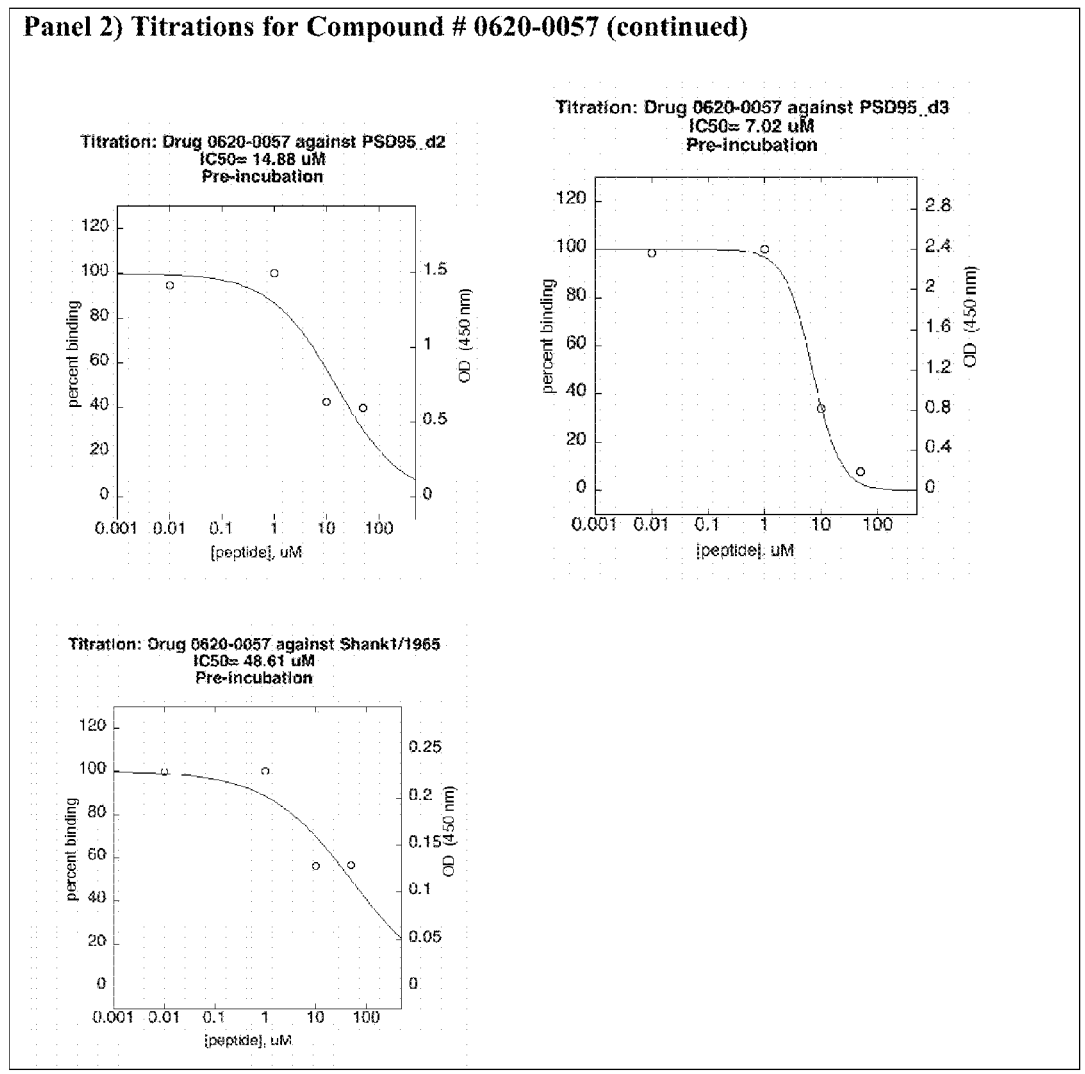
Figure 2B:
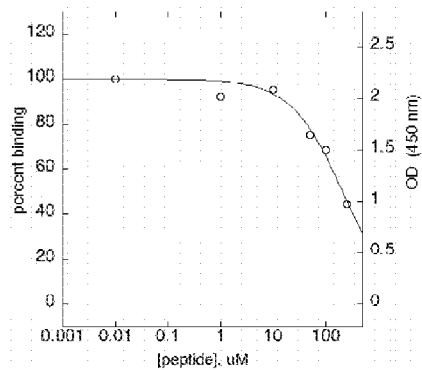
Figure 2B:
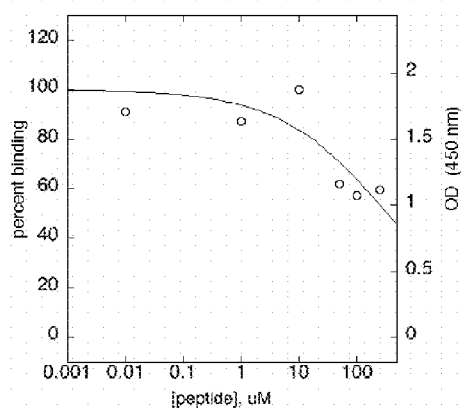
Figure 2B:
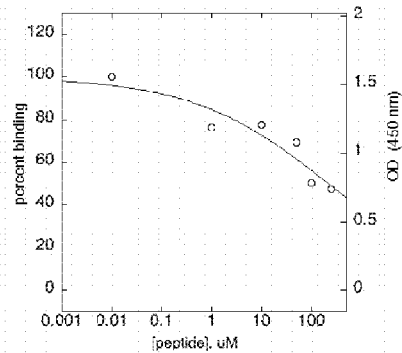
Figure 2B:
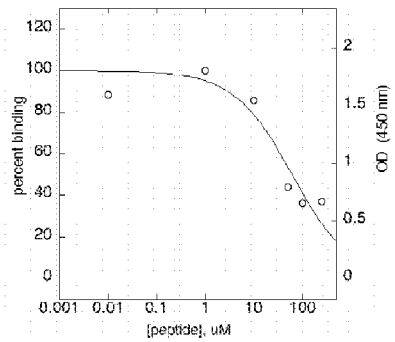
Figure 2B:
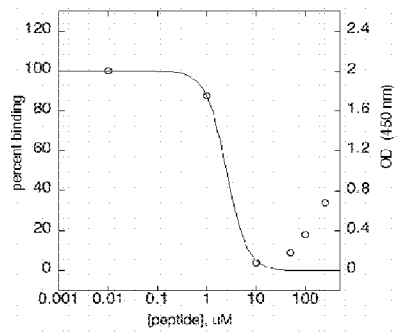
Figure 2B:
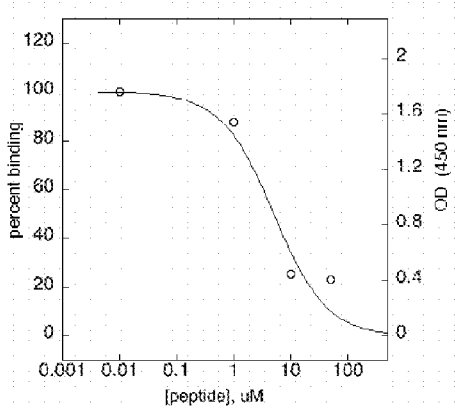
Figure 2B:
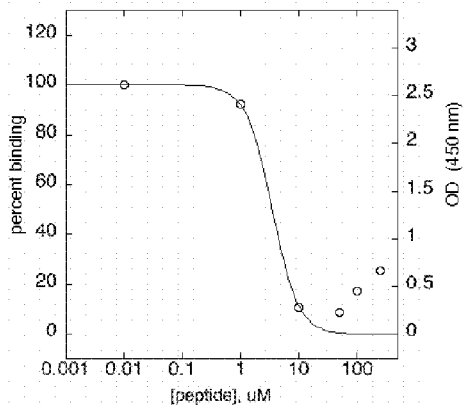
Figure 2B:
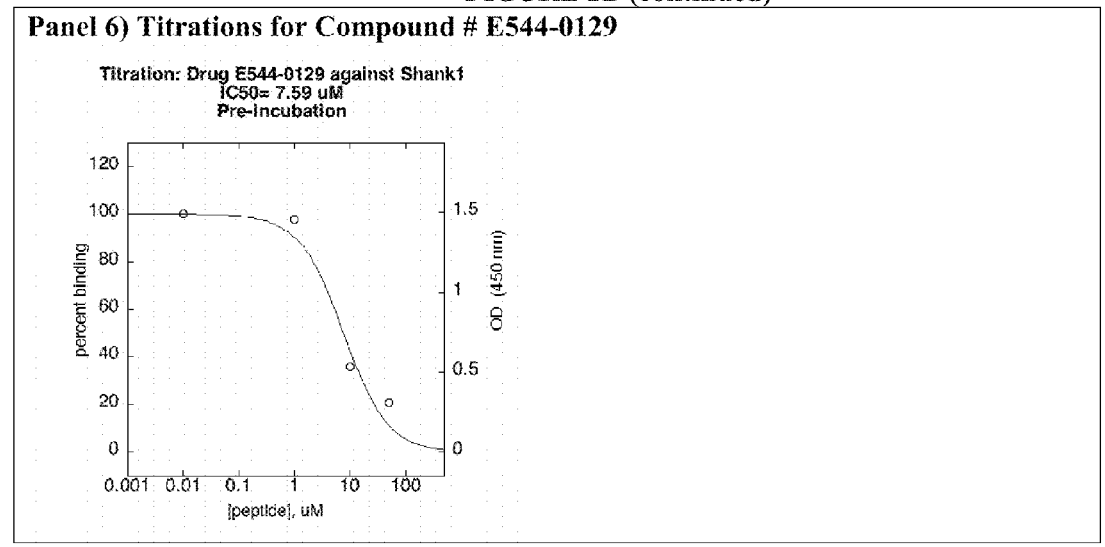

FIG. 2A—Chemical Structures of the Small Molecule Competitors of FIG. 1 and FIG. 2B.

FIG. 2B—Titration Analysis of Small Molecule Competitors Having Apparent IC50 values <250 μM:
(1) Titrations for Compound #3289-2331;
(2) Titrations for Compound #0620-0057;
(3) Titrations for Compound #C450-0454;
(4) Titrations for Compound #3558-0042;
(5) Titrations for Compound # MC 247808; and
(6) Titrations for Compound # E544-0129.

Figure 3A:
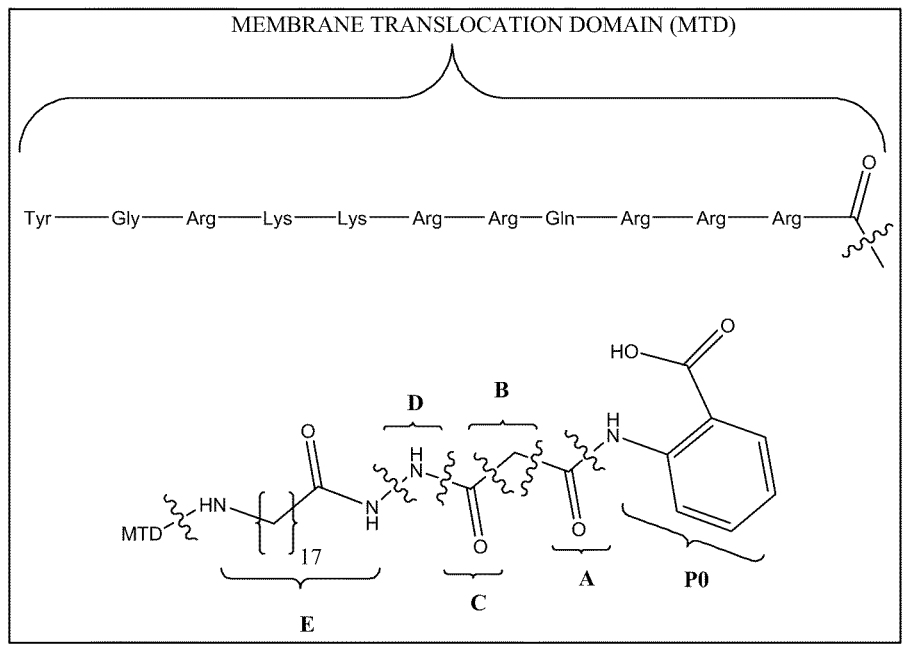

FIG. 3A—Small Molecule-Peptide Chimeric Conjugates: Membrane Translocation Domain Peptides Linked with Small Molecule Inhibitors.

Figure 3B:
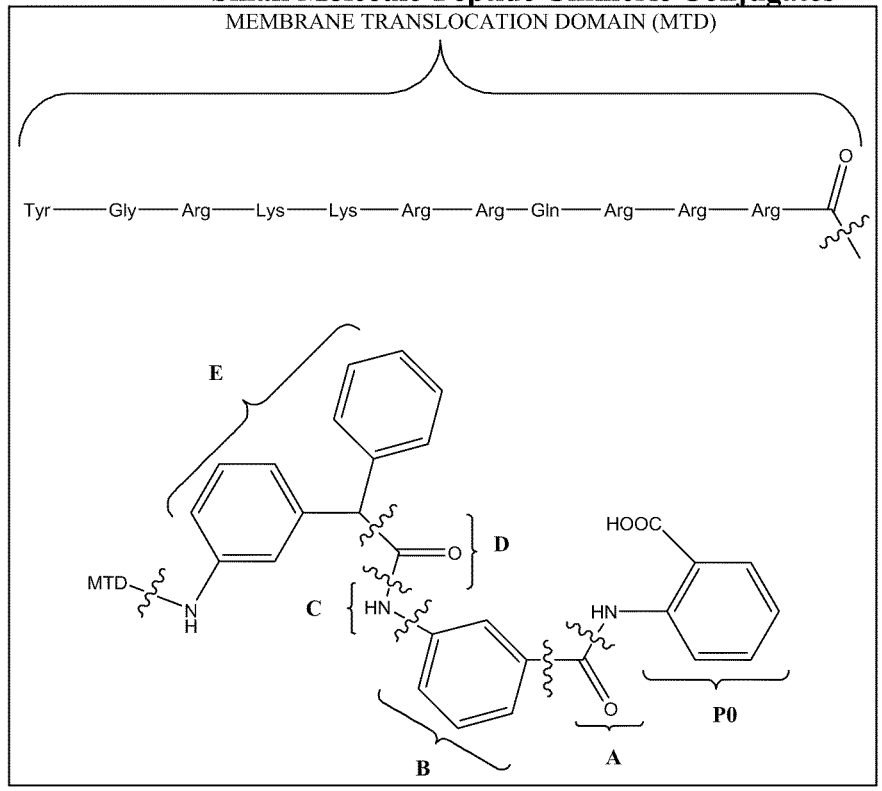

FIG. 3B—Small Molecule-Peptide Chimeric Conjugates: Membrane Translocation Domain Peptides Linked with Small Molecule Inhibitors.

Figure 4:
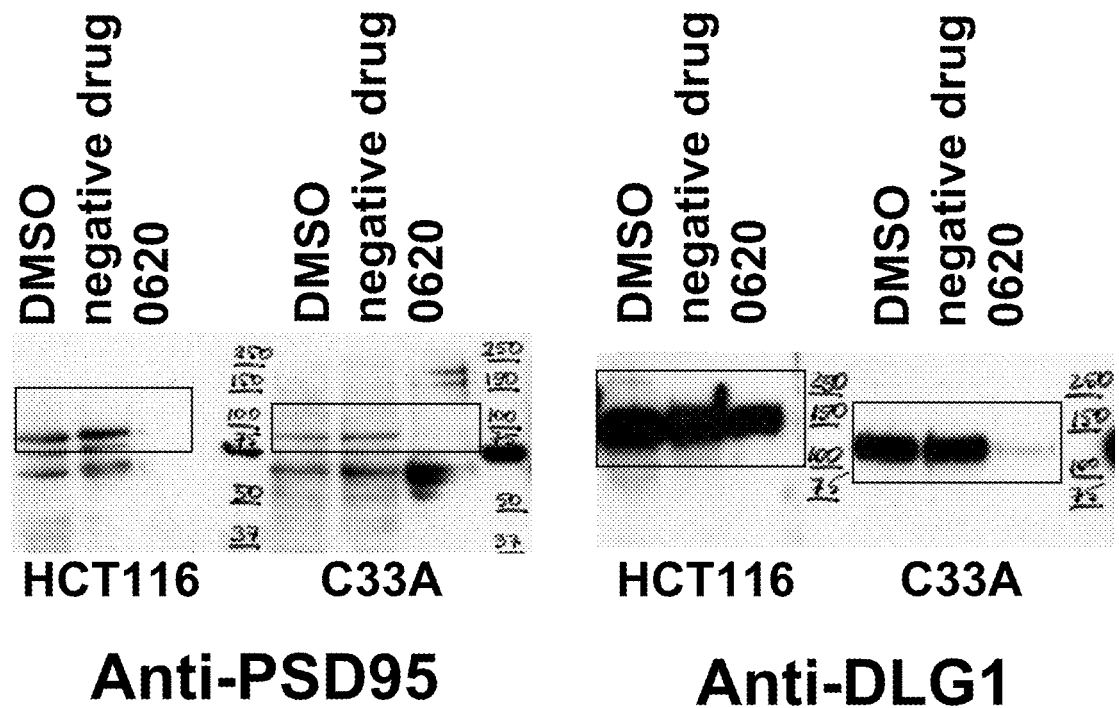

FIG. 4—PSD-95 Levels Are Reduced In the Presence of Compound 0620-0057.

Figure 5:
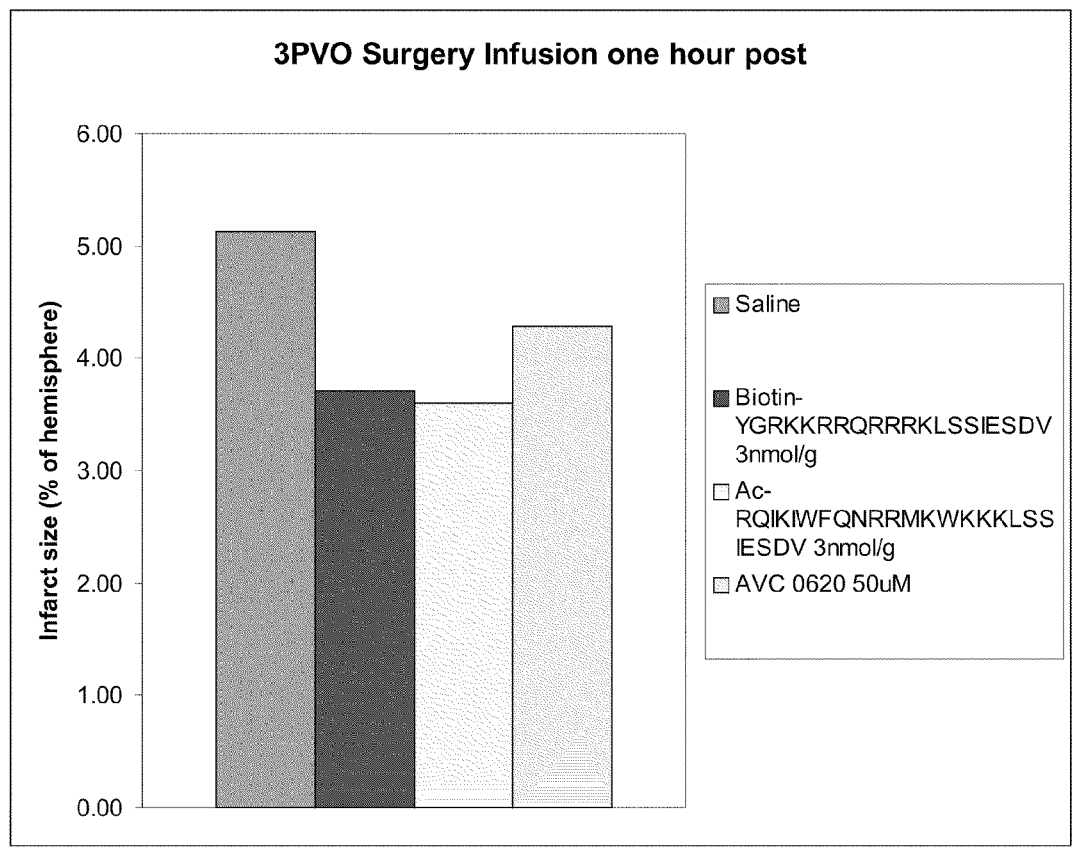

FIG. 5—Neuroprotective effect of Compound 0620-0057 in a mouse model of stroke in vivo

DETAILED DESCRIPTION OF THE PREFERRED EMBODIMENTS

I. The Present Invention

The present inventors used in silico screening with Accelrys software (Accelrys, San Diego, Calif.) to model and dock a 650,000 molecule library (ChemDiv, San Diego, Calif.; Blanca Pharmaceuticals, Mountain View, Calif.) with 4 different PDZ domain mimics. The best hits from in silico screening were subject to screening in a matrix/array competition assay format, i.e., assays where docking of ligands to solid phase PDZ domain in fusion proteins was assessed in the presence and absence of the small molecule competitor. The best of the hits in this latter analysis were then subject to titration binding studies, i.e., titration of the small molecule in the same competition assay to estimate an $IC_{50}$ value. Hits with $IC_{50}$ values of ≤250 μM were further examined in modeling studies designed to identify the common functional groups involved in binding interactions with PDZ proteins.

The compounds described herein are useful in several contexts. First, the inventors have already identified and cloned more than 255 PDZ domain proteins constituting more than 90% of the PDZ domains in proteins encoded by the human genome, and new PDZ proteins are constantly being discovered. In most cases, these PDZ domains have no known function. Thus, small molecule inhibitors are particularly useful in dissecting the role of these proteins in cyto and in vivo using standard pharmaceutical techniques. Also, as precise roles for known PDZ proteins continue to emerge, by using panels of different inhibitors, one can dissect what may turn out to be multiple roles for single PDZ proteins, or even PDZ families. It is also possible to more clearly define the binding requirements of each different PDZ and PDZ family using the herein described inhibitors, so as to be able to more accurately design "custom" inhibitors with very specific PDZ interactions. Finally, it is also possible to use the disclosed inhibitors to interfere with PDZ-related processes in vivo that are involved in disease states, i.e., for the treatment of disease.

More specifically, downregulation of PSD-95, a member of the PDZ family, is an important therapeutic effect for a number of diseases and disorders. Without limiting the field of use for such a drug, research has demonstrated that reduction of PSD-95 levels is neuroprotective in cellular and animal models of stroke. Sattler, 1999; Aarts, 2002, each of which is specifically incorporated by reference. Reduction of PSD-95 by antisense methods or knockout experiments has been demonstrated to reduce pain in multiple animal models. Tao et al., 2003; Garry, 2003, each of which is specifically incorporated by reference. It has also been shown to be correlated with improved outcomes for addiction. Roche, 2004; Yao, 2004 each of which is specifically incorporated by reference. PSD-95 can also be targeted for Alzheimer's disease and cardiovascular disorders through disruption of adrenergic receptor interactions.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). Although any methods and materials similar or equivalent to those described herein can be used in the practice or testing of the present invention, the preferred methods and materials are described. The following definitions are provided to assist the reader in the practice of the invention.

The term "modulation" as used herein refers to both upregulation, (i.e., activation or stimulation) for example by agonizing, and downregulation (i.e., inhibition or suppression) for example by antagonizing, a PDZ/PL interaction as measured by assessing a bioactivity (e.g., a binding activity). An inhibitor or agonist may cause partial or complete modulation of binding.

A "PDZ/PL inhibitor," used interchangeably with "PDZ/PL competitive inhibitor," is generally intended to mean that the subject compound reduces binding between a PDZ domain protein and a PDZ ligand by at least 20%, e.g., at least 30%, at least 40%, at least 50%, at least 60%, at least 70%, at least 80%, at least 90%, at least 95%, up to about 99% or 100%, as compared to controls that do not include the test compound. In general, agents of interest are those which exhibit $IC_{50}$ values in a particular assay in the range of about 1 mM or less. Compounds that exhibit lower $IC_{50}$s, for example, have values in the range of about 250 μM, 100 μM, 50 μM, 25 μM, 10 μM, 5 μM, 2 μM, 1 μM, 500 nM, 250 nM, 100 nM, 50 nM, 25 nM, 10 nM, 5 nM, 1 nM, or even lower, and compounds with these attributes are presently preferred.

As used herein, the term "acute insult to the central nervous system" includes short-term events that pose a substantial threat of neuronal damage mediated by glutamate excitotoxicity, as well as, longer-term propagation of stroke-induced ischemic damage mediated e.g. by inflammation. Ischemic events may also involve inadequate blood flow, such as a stroke or cardiac arrest, hypoxic events (involving inadequate oxygen supply, such as drowning, suffocation, or carbon monoxide poisoning), trauma to the brain or spinal cord (in the form of mechanical or similar injury), certain types of food poisoning which involve an excitotoxic poison such as domoic acid, and seizure-mediated neuronal degeneration, which includes certain types of severe epileptic seizures. It can also include trauma that occurs to another part of the body, if that trauma leads to sufficient blood loss to jeopardize blood flow to the brain (for example, as might occur following a shooting, stabbing, or automobile accident).

"Cardiovascular ischemia" is intended to mean acute and chronic damage in the circulatory system with cell death resulting, e.g., from hypoxia, e.g., heart attack, suffocation, carbon monoxide poisoning, trauma, pulmonary dysfunction and the like; decreased blood flow, e.g., from occlusion, atherosclerosis, diabetic microvascular insufficiency and the like; dysregulation of nitric oxide; dysfunction of the endothelium or vascular smooth muscle; and the like.

The term "analog" is used herein to refer to a small molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility in modulating a PDZ/PL interaction. Synthesis and screening of analogs, to identify variants of known compounds having improved traits (such as higher binding affinity, or higher selectivity of binding to a target and lower activity levels to non-target molecules) is an approach that is well known in pharmaceutical chemistry.

As used herein, "contacting" has its normal meaning and refers to bringing two or more agents into contact, e.g., by combining the two or more agents (e.g., two proteins, a protein and a small molecule, etc.). Contacting can occur in vitro, in situ or in vivo.

In most embodiments, the terms "polypeptide" and "protein" are used interchangeably. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids.

The term "fusion protein" or grammatical equivalents thereof references a non-natural protein, i.e., not occurring in the same form or purity in nature, composed of a plurality of polypeptide components from proteins that are not so-attached in their native state, e.g., polypeptides joined by their respective amino and carboxy-termini through a peptide linkage to form a single continuous polypeptide. Fusion proteins may be a combination of two, three or even four or more different proteins. Fusion proteins, include, but are not limited to, polypeptides having: heterologous amino acid sequences, fusions of heterologous and homologous leader sequences with or without N-terminal methionine residues; immunologically tagged proteins; and, signal generating fusion partners, e.g., fusion proteins including a fluorescent protein, β-galactosidase, luciferase, and the like.

"Peptides" are generally greater than 2 amino acids, greater than 4 amino acids, greater than about 10 amino acids, greater than about 20 amino acids, usually up to about 50 amino acids. In some embodiments, peptides are between 5 and 30 amino acids in length.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include PDZ polypeptides; antibody and receptor polypeptides; and aptamer polynucleotides and the like, for example antibodies, peptides or fragments of single stranded or double stranded DNA may employed.

The term "specific binding" refers to the ability of an agent to preferentially bind to a particular ligand compound in a mixture of different compounds. In certain embodiments, a specific binding interaction discriminates between desirable and undesirable ligands in a sample, in some embodiments the subject discriminatory activity is greater than about 10- to 100-fold or more (e.g., more than about 1000- or 10,000-fold). In certain embodiments, the affinity between a binding partner and the ligand compound when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, usually less than about $10^{-10}$ M. As used herein, "binding partners" and equivalents refer to pairs of molecules that can be found in an agent/ligand complex, i.e., exhibit specific binding with each other.

The phrase "surface-bound capture agent" refers to an agent that is immobilized on a surface of a solid substrate, where the substrate can have a variety of configurations, e.g., a sheet, bead, stick, or other structure, such as a plate with wells. In certain embodiments, the collections of capture agents employed herein are present on a surface of the same support, e.g., in the form of an array.

"Isolated" or "purified" generally refers to a chemical form of an agent that is not present in nature, e.g., a sample preparation in which a substance (small molecule compound, polynucleotide, protein, polypeptide, peptide) comprises a significant percent (e.g., greater than 2%, greater than 5%, greater than 10%, greater than 20%, greater than 50%, greater than 75%, greater than 80%, greater than 85%, greater than 90%, greater than 95%, 96%, 97%, 98%, 99% or 99.5% or more) of the subject sample in which it resides. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found in nature.

The term "assessing" includes any form of measurement, and includes determining if an element is present or not. The terms "determining," "measuring," "evaluating," "assessing" and "assaying" are used interchangeably and may include quantitative and/or qualitative determinations. Assessing may be relative or absolute. "Assessing binding" includes, e.g., determining the amount of binding, the $K_D$ for binding affinity and/or determining whether binding has occurred (i.e., whether binding is present or absent).

The terms "treatment," "treating," "treat," and the like, refer to obtaining a desired pharmacologic and/or physiologic effect. The effect may be prophylactic in terms of partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing, regression of the disease and/or relieving one or more disease symptoms. "Treatment" is also meant to encompass delivery of an agent in order to provide for a pharmacologic effect, even in the absence of a disease or condition.

"Subject," "individual," "host" and "patient" are used interchangeably herein, to refer to an animal, human or non-human, amenable to a treatment according to a method of the invention. Generally, the subject is a mammalian subject. Exemplary subjects include, but are not necessarily limited to, humans, domestic and non-domestic animals: e.g., non-human primates, mice, rats, cattle, sheep, goats, pigs, dogs, cats, and horses; with humans being of particular interest.

Various biochemical and molecular biology methods referred to herein are well known in the art, and are described in, for example, Sambrook et al. (1989) and Ausubel et al. (1987-1999).

An "alkyl" group refers to a saturated aliphatic hydrocarbon, including straight-chain, branched chain, and cyclic alkyl groups. Alkyl groups can comprise any combination of acyclic and cyclic subunits. Further, the term "alkyl" as used herein expressly includes saturated groups as well as unsaturated groups. Unsaturated groups contain one or more (e.g., one, two, or three), double bonds and/or triple bonds. The term "alkyl" includes substituted and unsubstituted alkyl groups. "Lower alkyl" is defined as having 1-7 carbons. Preferably, the alkyl group has 1 to 18 carbons and is straight-chain or branched.

An "alkenyl" group refers to an unsaturated hydrocarbon group containing at least one carbon-carbon double bond, including straight-chain, branched-chain, and cyclic groups. Preferably, the alkenyl group has 1 to 18 carbons. The alkenyl group may be substituted or unsubstituted.

An "alkynyl" group refers to an unsaturated hydrocarbon group containing at least one carbon-carbon triple bond, including straight-chain, branched chain, and cyclic groups. Preferably, the alkynyl group has 1 to 18 carbons. The alkynyl group may be substituted or unsubstituted.

An "alkoxy" group refers to an "—O-alkyl" group, where "alkyl" is defined above.

III. PDZ Proteins

PDZ proteins are named for the first letter of the first three proteins in the family to be discovered (PSD-95, DLG, and ZO-1). These proteins initiate and regulate the assembly of macromolecular protein complexes including, e.g., complexes of membrane proteins; cytoskeletal proteins; signaling enzymes such as kinases; ion channel proteins such as sodium, potassium and calcium channels; and other proteins. PDZ proteins are characterized by PDZ domains containing ~80-90 residues that fold into a hydrophobic cleft structure with a β-sandwich of 5-6 β-strands and two α-helices, also referred to herein as a "PDZ groove." Natural PDZ ligands are peptides that bind into the latter hydrophobic cleft composed of a β-strand (βB), an α-helix and a loop that binds the peptide carboxylate group. Natural peptides generally bind to the PDZ groove in an anti-parallel fashion to the βB strand, with the C-terminal residue occupying a hydrophobic pocket. PDZ heterodimers form a linear head-to-tail arrangement that involves recognition of an internal on one of the partner proteins. PDZ domains are recognized as families by the National Center for Biotechnology Information (see, e.g., the world wide web at .ncbi.gov), e.g., in Pfam.

PDZ domains bind to PDZ ligand (PL) amino acid sequences which often comprise the C-terminal 4-9 residues of proteins. The consensus binding sequence in these PL commonly contains a hydrophobic residue, commonly Val or Ile, at the C-terminus. Fanning & Anderson (1999) instituted a system for numbering the positions in a PL, i.e., starting at the C-terminus with position zero, i.e., P(0), and proceeding in increasing negative numbers toward the N-terminus, e.g., the residues of an illustrative peptide are P(0)-Val, P(−1)-Xaa, P(−2)-Ser or Thr, P(−3)-Xaa. The latter "X(S/T)XV" sequence is referred to as a class I PL motif. Residues at the −2 and −3 positions are important in determining specificity. Representative examples of proteins with PDZ domains are set forth in prior patent applications filed by certain of the inventors (below) which are included herein by reference, and include putative targets for the inhibitors of the present application: Mint-1, Mint2, Mint3, CSKP, Dig, Dig2, Dig1, Dig4, DVL1, DVL3, DVLL, GIPC, HtrA2, LIMK2, MPP2, NEB1, OMP25, hCLIM1, PTPH1, ZO-2, hPTP1E, hPTP1E, INADL, RGS12, RIL, ZO-1, ZO-2, GST, NOS1, LNX1, IL16 (2), SDB1, NHERF, E3KARP, PALS1, KIAA0300, KIAA0303, KIAA0316, KIAA0559, KIAA0613, KIAA1719, MAST205, Magi1, Magi3, BAI1, AIP1, PTPN4, GRIP1, SCRIB1, PARD3, HARM, MLL4, TIP1, SDB2, Shank, MUPP1, DLG3, DLG5, DLG2, NeDLG1, PAR6B, LIK1, LOMP, RIL, A2LIM, TIAM1, LIN7C, LIN7B, LIN7A, GEF11, GEF12, PDZK, SNB1, SNA1, SHK1, MPP6, PIST, GEF2, PSD95 and RIM2.

IV. PDZ Ligands and Binding Assays

A. Ligands

Illustrative PDZ ligands and binding assays have been disclosed previously by certain of the inventors in, e.g., PCT/US01/32202 (filed Oct. 15, 2001); PCT/US01/44138 (filed Nov. 9, 2001); PCT/US02/24655 (filed Aug. 2, 2002); PCT/US03/28508 (filed Sep. 9, 2003); PCT/US04/011195 (filed Apr. 12, 2004); and U.S. Pat. No. 6,942,981 (issued Oct. 13, 2005), all of which are incorporated herein by reference in their entirety.

B. Assays

Binding of the PDZ polypeptides may be assayed using methods that are well known in the art. For example, binding may be assayed biochemically, or, in other embodiments, the two proteins may be assayed by detecting a signal that is only produced when the proteins are bound together. In testing candidate agents, such a signal can be evaluated in order to assess binding between the two proteins. For example, as used in the subject assays, the polypeptides may form a fluorescence resonance energy transfer (FRET) system, bioluminescence resonance energy transfer (BRET) system, or colorimetric signal producing system that can be assayed. The assays here involved a polypeptide containing the PDZ domain and a PDZ ligand. In certain embodiments, at least one of the polypeptides may be a fusion protein that facilitates detection of binding between the polypeptides. Accordingly one of the polypeptides may contain, for example, an affinity tag domain or an optically detectable reporter domain.

Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, etc. Suitable affinity tags also include domains for which, binding substrates are known, e.g., HIS, GST and MBP tags, etc., and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g., the IgG Fc receptor.

Suitable reporter domains include any domain that can optically report the presence of a polypeptide, e.g., by emitting light or generating a color. Suitable light emitting reporter domains include luciferase (from, e.g., firefly, *Vargula, Renilla reniformis* or *Renilla muelleri*), or light emitting variants thereof. Other suitable reporter domains include fluorescent proteins, (from, e.g., jellyfish, corals and other coelenterates as such those from *Aequoria, Renilla, Ptilosarcus, Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase. In some preferred embodiments, the reporter domain is *Renilla* luciferase (e.g., pRLCMV; Promega, cat. no. E2661).

Also as is known in the art, an affinity tag or a reporter domain may be present at any position in a polypeptide of interest. However, in certain embodiments, they are present at the N-terminal end; or, in a non-C-terminal; or, in a non-interfering portion of a PDZ protein or PL.

In particular embodiments, one or both of the polypeptides may contain a tag or reporter. For example, if FRET or BRET methods are employed, the polypeptides may both be tagged using different autofluorescent polypeptides.

In certain specific embodiments, the PDZ domain-containing polypeptide contains at least the PDZ domain from Shank-1, Shank-2 or Shank-3, which PDZ domains each bind to the PDZ ligand of COX. The Shank PDZ domain may contain the PDZ domain of a "wild-type" Shank polypeptide, or a variant thereof that retains ability to bind to the PDZ ligand of COX.

The Shank-1 and Shank-2 and Shank-3 polypeptides and encoding cDNAs are deposited in the GenBank database as GID NOS: 7025450 and 6049185, respectively, whereas the coding sequence for Shank-3 is encoded by GenBank accession no. XM_037493 (gi: 51476100).

Another PDZ domain-containing polypeptide contains at least the PDZ domain from Mast-205, which PDZ domains binds to the PDZ ligand of COX, TLR4 and NMDA receptor 2B. The Mast205 PDZ domain may contain the PDZ domain of a "wild-type" Mast-205 polypeptide, or a variant thereof that retains ability to bind to the PDZ ligand. The Mast-205 polypeptide and encoding cDNA are deposited in the GenBank database as accession no. KIAA0807.

Variant polypeptides are readily designed since the PDZ domain of several proteins are relatively well characterized at the crystal and NMR structural level. For example, the three-dimensional structure of a PDZ domain is described and discussed in Doyle (1996) and a crystal structure of Shank-1 bound to the PDZ ligand domain of guanylate kinase-associated protein (GKAP1a) has been reported. Variants are generally at least 80% identical, at least 90% identical, at least 95% identical or, in certain embodiments at least 98% or at least 99% identical to a wild-type PDZ domain amino acid sequence. In other words, as employed in a method described herein, a PDZ domain-containing polypeptide may contain at least 1, 2, 3, 4, or 5 or more and in certain embodiments up to 10 amino acid substitutions, as compared to a wild-type sequence. A substitution may be conservative (i.e., replacing one amino acid with another within the following groups: gly, ala; val, ile, leu; asp, glu; asn, gln; ser, thr; lys, arg; and phe, tyr), or non-conservative. Shank PDZ domains binding COX are similar in sequence, e.g., the Shank-1 and Shank-2 PDZ domains are approximately 85% identical; the Shank-1 and Shank-3 PDZ domains are approximately 79% identical; and, the Shank-2 and Shank-3 PDZ domains are approximately 80% identical. Thus, a variety of non-natural Shank derivatives may be constructed, e.g., by substituting amino acids from one sequence into another.

When a particular PDZ domain-containing polypeptide is referenced herein, e.g., when a reference is made to a Shank-1, Shank-2, Shank-3 or Mast-205 PDZ domain-containing polypeptide, the reference is intended to encompass polypeptides containing a wild-type PDZ domain, as well as, all variants thereof that retain PDZ ligand binding activity.

PDZ polypeptides and PL peptides may be made synthetically (i.e., using a machine) or using recombinant means, as is known in the art. Methods and conditions for expression of recombinant proteins are well known in the art. See, e.g., Sambrook (2000), and Ausubel, (1999). Typically, polynucleotides encoding the polypeptides used in the invention are expressed using expression vectors. Expression vectors typically include transcriptional and/or translational control signals (e.g., the promoter, ribosome-binding site, and ATG initiation codon). In addition, the efficiency of expression can be enhanced by the inclusion of enhancers appropriate to the cell system in use. For example, the SV40 enhancer or CMV enhancer can be used to increase expression in mammalian host cells. Typically, DNA encoding a polypeptide of the invention is inserted into DNA constructs capable of introduction into and expression in an in vitro host cell, such as a bacterial (e.g., *E. coli, Bacillus subtilus*), yeast (e.g., *Saccharomyces*), insect (e.g., *Spodoptera frugiperda*), or mammalian cell culture systems. Mammalian cell systems are preferred for many applications. Examples of mammalian cell culture systems useful for expression and production of the polypeptides of the present invention include HEK293 cells (human embryonic kidney line); CHO cells (Chinese hamster ovary); HeLa human cervical carcinoma (Helen Lane) cells, and others known in the art. The use of mammalian tissue cell culture to express polypeptides is discussed generally in Winnacker, FROM GENES TO CLONES (VCH Publishers, N.Y., N.Y., 1987) and Ausubel (1999). In some embodiments, promoters from mammalian genes or from mammalian viruses are used, e.g., for expression in mammalian cell lines. Suitable promoters can be constitutive, cell type-specific, stage-specific, and/or modulatable or regulatable (e.g., by hormones such as glucocorticoids). Useful promoters include, but are not limited to, the metallothionein promoter, the constitutive adenovirus major late promoter, the dexamethasone-inducible MMTV promoter, the SV40 promoter, and promoter-enhancer combinations known in the art.

As noted above, the subject assay may be performed in vitro (i.e., in which the polypeptides are present in a solution a not in a cell) or in a cellular environment (in which the polypeptides are present in a cell), or in a test animal, e.g., a mouse, in vivo.

i. In Vitro Assays

In vitro assays may be performed using a variety of platforms that are known in the art and have also been disclosed previously by certain of the inventors e.g. in PCT/US01/32202 (filed Oct. 15, 2001); PCT/US01/44138 (filed Nov. 9, 2001); PCT/US02/24655 (filed Aug. 2, 2002); PCT/US03/28508 (filed Sep. 9, 2003); PCT/US04/011195 (filed Apr. 12, 2004); and U.S. Pat. No. 6,942,981 (issued Oct. 13, 2005), all of which are incorporated herein by reference in their entirety. In certain embodiments, the methods involve linking, either covalently or non-covalently, a first agent (either a PDZ domain polypeptide or a PDZ ligand) to a substrate, contacting the substrate-bound agent with a cognate binding partner (PDZ ligand or domain), and detecting the presence or amount of the bound partner. For competition assays, the method may be performed in the presence of a test compound. In embodiments in which the cognate binding partner is detectably labeled (e.g., as an optically-detectable fusion protein), the presence or amount of the bound partner is quantified by detecting the label.

A "substrate" is intended to mean a solid, semi-solid, or insoluble support as may be constructed from any material appropriate for linkage to a polypeptide, peptide or small molecule compound. Useful substrates do not interfere with the detection of bound partner. As will be appreciated by those in the art, the number of possible substrates is large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, ceramics, and a variety of other polymers. In one embodiment, the substrates allow optical detection and do not themselves appreciably fluoresce or emit light. In addition, as is known the art, the substrate may be coated with any number of materials, including polymers, such as dextrans, acrylamides, gelatins, agarose, biocompatible substances such as proteins including bovine and other mammalian serum albumin.

The substrate may optionally be coated with an agent to facilitate binding of an agent to the substrate. For example, as set forth further below in the Examples section, substrates may be coated with biotinylated peptides, detectable using enzyme-labeled streptavidin. Alternatively, antibody specific for a PDZ fusion protein is attached to a substrate and the PDZ protein is attached to the substrate through the antibody, e.g., anti-GST to attach GST-PDZ fusion proteins.

In embodiments where the PDZ ligand is attached to a signal generating reporter, the ligand may be detected by detecting reporter activity. Methods of determining reporter activity, e.g., luciferase and GFP activity, are generally well known in the art (e.g., Ramsay et al., 2001). Detection of a bound PDZ or PL partner in an assay may also be accomplished using an antibody, e.g., a labeled antibody. Methods for detecting polypeptides using antibodies are known in the art (e.g., Ausubel et al., 1999; Harlow et al., Antibodies: A Laboratory Manual, 1$^{st}$ Ed. 1988 Cold Spring Harbor, N.Y.).

Two complementary assays, termed "A" and "G," have been developed by certain of the inventors to detect modulation of binding between a PDZ-domain polypeptide and PDZ ligands, e.g., as disclosed in PCT/US01/32202 (filed Oct. 15, 2001); PCT/US01/44138 (filed Nov. 9, 2001); PCT/US02/24655 (filed Aug. 2, 2002); PCT/US03/28508 (filed Sep. 9, 2003); PCT/US04/011195 (filed Apr. 12, 2004); and U.S. Pat. No. 6,942,981 (issued Oct. 13, 2005), all of which are incorporated herein by reference in their entirety. In each of the two different assays, binding is detected between a peptide mimetic of a putative C-terminal PL sequence (i.e., a candidate PL peptide) and a PDZ-domain polypeptide (typically a fusion protein containing a PDZ domain). In the "A" assay, the PL peptide is immobilized and binding of a soluble PDZ-domain polypeptide to the immobilized peptide is detected in the presence or absence of a test compound. In the "G" assay, the PDZ-domain polypeptide is immobilized and binding of a soluble PL peptide is detected in the presence or absence of a test compound. However, it will be appreciated by ordinarily skilled practitioners that these assays can be modified while remaining useful for the purposes of the present invention. Details of these assays are also set forth in U.S. Ser. No. 10/630,590, filed Jul. 29, 2003, published as US/2004/0018487. A variant of the "G-assay" involving a solid-phase competitive assay format for identifying small molecule inhibitors of PDZ:PL interactions is disclosed below in Examples, below.

ii. Cellular Assays

Cellular assays generally involve co-producing (i.e., producing in the same cell, regardless of the time at which they are produced), PL and PDZ polypeptides using recombinant DNA. Commonly, the binding interaction of a PL and a PDZ in the cell is detected using a reporter. Suitable cells for producing the polypeptides including PDZ domains and ligands include prokaryotic, e.g., bacterial cells, as well as eukaryotic cells, e.g., an animal cell (for example an insect, mammal, fish, amphibian, bird or reptile cell), a plant cell (for example a maize or *Arabidopsis* cell), or a fungal cell (for example a *S. cerevisiae* cell). Any cell suitable for expression of subject polypeptide-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293); HEK-293T cells; baby hamster kidney cells (BHK, ATCC CCL 10); chinese hamster ovary-cells (CHO); mouse sertoli cells (TM4); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells; NIH/3T3 cells (ATCC CRL-1658); and mouse L cells (ATCC CCL-1). Additional cell lines will become apparent to those of ordinary skill in the art, such as those available from the American Type Culture Collection, 10801 University Boulevard, Manassas, Va. 20110-2209.

In particular embodiments, neuronal cells, e.g., SHSY5Y (neuroblastoma cell line), hippocampal murine HT-22 cells, primary cultures from astrocytes, cerebral cortical neuronal-astrocytic co-cultures, mixed neuronal/glial hippocampal cultures, cerebellar granular neuronal cell cultures or primary neuronal cultures derived from rat cortex (E15-17) may be employed.

A variety of different reporter platforms may be employed to detect a binding interaction between a PL and PDZ in a cell, as well as, interference with a PDZ/PL interaction in a cell, e.g., yeast "two-hybrid" methods and, fluorescence-based FRET or BRET-based methods. In general, in competition assay these methods involve contacting a cell that produces the subject PDZ and PL polypeptides with a test agent, and determining if the test agent has any effect on PDZ/PL binding interactions.

In another reporter platform the GAL4 system is used to screen test agents for those capable of modulating PDZ/PL binding interactions. Such methods may employ a vector (or vector system) encoding two or more polypeptides: e.g. a DNA binding fusion protein that contains a PDZ or a PL linked to a DNA transcription activator. In the latter case, the PDZ/PL binding interaction activates expression of a reporter gene or selectable marker, e.g., an enzymatic reporter. The levels of enzymatic reporters like α- or β-galactosidase or β-lactamase are measured by quantifying enzymatic activity using, e.g., colorimetric substrates, (orthomethylphenylthiogalactoside; OMTP), or X-gal where the fluorescence is assessed photometrically. Combinatorial approaches may also be used to assess pools of test agents. Such methods are known in the art.

In another exemplary embodiment, Fluorescence Resonance Energy Transfer (FRET) may be used to detect binding between PDZ and PL polypeptides in a cell. In such binding assays, the fluorescent reporter molecules commonly have overlapping spectral properties such that the emission of a donor molecule overlaps with the excitation spectra of an acceptor molecule. The latter donor molecule is thereby excited and emits the absorbed energy as fluorescent light. In competition assay formats, the fluorescent energy of the donor molecule is either quenched by the test molecule or energy transfer between the donor and acceptor is inhibited. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects may be diminished or eliminated (U.S. Pat. No. 5,981,200).

Reporter platforms may also involve uses of a Bioluminescence Resonance Energy Transfer (BRET) system. In one such test assay a BRET system comprises a luciferase from *Renilla* and a GFP. In one embodiment, a BRET system comprises a luciferase from *Renilla* and a GFP. Exemplary BRET methodologies are described in Kroeger et al. (2001) and Xu et al. (1999).

Optionally, active compounds of the invention can also be screened for capacity to inhibit interactions between PSD-95 and NMDAR 2B using assays described in e.g., US 20050059597. Useful compounds typically have IC50 values of less than 50 uM, 25 μM, 10 μM, 0.1 μM or 0.01 μM in such an assay. Preferred compounds typically have an IC50 value of between 0.001-1 μM, and more preferably 0.05-0.5 or 0.05 to 0.1 μM.

iii. Animal Models

The activity of small molecule compounds of the invention, can be tested in various animal models of stroke. In one such model, adult male Sprague-Dawley rats are subjected to transient middle cerebral artery occlusion (MCAO) for 90 minutes by the intraluminal suture method (36,37). Animals are fasted overnight and injected with atropine sulfate (0.5 mg/kg IP). After 10 minutes anesthesia is induced. Rats are orally intubated, mechanically ventilated, and paralyzed with pancuronium bromide (0.6 mg/kg IV). Body temperature is maintained at 36.5-37.5° C. with a heating lamp. Polyethylene catheters in the femoral artery and vein are used to continuously record blood pressure and to sample blood for gas and pH measurements. Transient MCAO is achieved for 90 min by introducing a poly-L-lysine-coated 3-0 monofilament nylon suture (Harvard Apparatus) into the circle of Willis via the internal carotid artery, effectively occluding the middle cerebral artery. This produces an extensive infarction encompassing the cerebral cortex and basal ganglia. Animals are treated with either a test compound or a negative or positive control. Treatment can be either before or up to one hour after inducing ischemia. A negative control can be vehicle. A positive control can be Tat-NR2B9c, previously shown to be effective in 60/904,507 filed Mar. 2, 2007, herein incorporated by reference. The test compound is delivered by a single intravenous bolus injection 45 min prior to MCAO (3 nmoles/g). After administering test compound to the animals, infarction volume and/or disability index are determined. Infarction volumes are usually determined 24 hr post treatment but can be determined at a later time such as 3, 7, 14 or 60 days. Disability index can be monitored over time, e.g., at 2 hr post treatment, 24 hr post treatment, one week and one month post treatment. A test compound showing a statistically significant reduction in infarction volume and/or disability index relative to control animals not treated with the test compound are identified as having activity useful for practicing the methods of the invention.

Similar experiments can be performed in animal subject to permanent ischemia. Permanent ischemia of the middle cerebral artery pial vessel can be carried out as described by Forder et al., Am J Physiol Heart Circ Physiol 288:H1989-H1996 (2005). In brief, the right ECA is cannulated with PE 10 polyethylene tubing. The skull is exposed via a midline incision, and a 6- to 8-mm cranial window is made over the right somatosensory cortex (2 mm caudal and 5 mm lateral to bregma). The pial arteries are visualized by injecting small boluses (10-20 μL) of the vital dye patent blue violet (10 mMol/L; Sigma) in normal saline, into the ECA. The same three pial arteriolar MCA branches are electrically cauterized and dye injections are repeated to ensure the interruption of flow through the cauterized arterioles. The incision is then closed and the animal returned to its cage and allowed free access to food and water. This permanent ischemia model produces a highly reproducible small infarction limited to the cortex underlying the coagulated terminal pial arteries.

The left middle cerebral artery can be occluded by the intraluminal suture method described by Longa, Stroke 20, 84-91 (1989). In brief, the left common carotid artery (CCA) is exposed through a midline neck incision and is dissected free from surrounding nerves and fascia, from its bifurcation to the base of the skull. The occipital artery branches of the external carotid artery (ECA) are then isolated, and these branches dissected and coagulated. The ECA is dissected further distally and coagulated along with the terminal lingual and maxillary artery branches, which are then divided. The internal carotid artery (ICA) is isolated and separated from the adjacent vagus nerve, and the pterygopalatine artery is ligated close to its origin. The tip of a 4-cm length of 3-0 monofilament nylon suture (Harvard Apparatus) is rounded by burning to achieve a tip diameter of 0.33-0.36 mm and tip length of 0.5-0.6 mm and coated with poly-L-lysine (Belayev et al., 1996). The suture is introduced through the CCA and advanced into the ICA and thence into the circle of Willis (about 18-20 mm from the carotid bifurcation), effectively occluding the middle cerebral artery. The silk suture around the CCA is tightened around the intraluminal nylon suture to secure it and permanently occlude the middle cerebral artery.

The distal middle cerebral artery pial vessels can be occluded as described elsewhere (Forder et al., 2005). In brief, the right ECA is cannulated with PE 10 polyethylene tubing. The skull is exposed via a midline incision, and a 6- to 8-mm cranial window is made over the right somatosensory cortex (2 mm caudal and 5 mm lateral to bregma). The pial arteries are visualized by injecting small boluses (10-20 μL) of the vital dye patent blue violet (10 mMol/L; Sigma) in normal saline, into the ECA. The same three pial arteriolar MCA branches are electrically cauterized and dye injections are repeated to ensure the interruption of flow through the cauterized arterioles. The incision is then closed and the animal returned to its cage and allowed free access to food and water. This permanent ischemia model produces a highly reproducible (Forder et al., 2005) small infarction that is limited to the cortex underlying the coagulated terminal pial arteries.

V. Inhibitors of PDZ Interactions

A. Rational Drug Design

The goal of rational drug design is to design structural analogs of biologically active compounds. By constructing such analogs, it is possible to fashion drugs that are more active or stable than the natural molecules; or, that have different susceptibility to alteration; or, that exhibit different degrees of absolute specificity or binding affinity.

Generally, the three-dimensional structure of a molecule is determined using methods such as X-ray crystallography or nuclear magnetic resonance spectroscopy. While these methods represent only non-predictive approximations of the liquid structure of a protein, it is possible, armed with this information, for researchers using powerful computer programs to search through databases containing the structures of many different chemical compounds. The computer and investigator can thus select those compounds that are may be most likely to interact with the receptor, and these can subsequently be tested in the laboratory. In practice, as illustrated in the Examples section below, successful application of these methods are time consuming often requiring patience, experience and a good deal of intuition.

If an interacting compound cannot be found, other program can be used that attempt, from first principles, to design molecules that are likely to interact with the target. One can then perform additional databases searches to identify compounds with similar properties to the designed molecules, or one can synthesize the designed molecules which can be screened for activity.

B. Known PDZ Inhibitors

Aarts et al. (2002) disclosed peptide-based inhibitors of the interaction between NMDA receptors and intracellular PSD95 PDZ proteins, as well as, their uses in animal models of stroke. The latter compounds when administered after induction of stroke effectively decreased the total area of ischemia in the brain of experimental animals. One of these compounds is presently in preclinical trials under an US FDA- and Canadian CTA-approved protocol. Human trials are expected next year.

Known features of PDZ interactions with PL in cells are useful for identifying clinical targets and subjects who would benefit from therapeutic intervention using the instant small molecules. For example, the instant compounds may be used in therapeutic modalities in patients with cancer and CNS disease. In particular, PDZ protein's have key roles in disease processes and thus, blocking these PDZ/PL interactions using small molecule inhibitors may lead to clinical benefits. Findings supportive of this general notion are as follows, namely, 1) Blocking PDZ/PDZ Ligand (PL) interactions in cancer cells, e.g. as follows: namely,
   a. In colorectal cancer cells, the TIP1 PDZ protein interacts with a PL motif in β-catenin and changes cell proliferation and anchorage independent growth. (Kanamori, 2003). Thus, therapies employing small molecule inhibitors of the latter PDZ/PL interactions constitute useful modalities in treatments of colorectal cancers;
   b. In hepatocellular carcinoma cells, the EPB50 PDZ protein interacts with a PL motif in β-catenin and the interaction may increase β-catenin-mediated TCF-dependent transcription leading to increased oncogene transcription (Shibata et al., 2003). Thus, small molecule inhibitors which block the PDZ/PL interactions of β-catenin with this, and other PDZ binding partners such as Magi1, can be used in therapies to inhibit the Wnt pathway; decrease cell proliferation; and/or, induce apoptosis in tumor cells. The latter effects on hepatocellular carcinoma cells constitutes a useful strategy in treatments for this aggressive cancer;
   c. In adult T-cell leukemia induced by HTLV-1, the PDZ protein TIP 1 interacts with a PL motif in the Tax viral oncoprotein and this interaction may: (i) promote malignant transformation of HTLV-1 infected cells (Hirata et al., 2004); and, (ii) increase virus mediated T-cell proliferation and persistence (Xie et al., 2005). Thus, small molecule inhibitors of TIP/Tax PDZ/PL interactions can decrease cell proliferation and malignant transformation. The latter intervention constitutes a useful strategy in treatment modalities for adult T-cell HTLV-1 induced leukemia;
   d. In cervical cancer induced by human papilloma virus (HPV), the PDZ proteins TIP 1 and hDlg interact with a PL motif in HPV E6 or E6 oncoprotein, and these PDZ/PL interactions may promote cell motility in cervical cancer cells (Hampson et al., 2004; Du et al., 2005). Thus, small molecule inhibitors that inhibit the TIP/E6 or hDlg/E6 PDZ/PL interaction may decrease cell motility and metastasis. This intervention constitutes a useful therapeutic strategy in treatments of cervical cancer;
   e. Also in cervical cancer, the PDZ protein Magi-1 domain1 binds to a PL motif in the HPV E6 or E6 oncoprotein, and this PDZ/PL interaction may promote tumor cell migration by preventing Magi1-d1 degradation. Thus, small molecule inhibitors that interfere with the Magi-1/E6 PDZ/PL interaction can restore Magi1 levels, i.e., inhibiting cell migration and metastasis in cervical cancer. The latter intervention constitutes a useful therapeutic strategy in treatments to prevent metastasis in cervical and ovarian cancer;
   f. In Adenovirus-associated breast cancer, the PDZ protein Magi-1 interacts with a PL motif in the E4-ORF1 oncoprotein resulting in loss of cell polarity and growth controls (Latorre, et al., 2005). Thus, small molecule inhibitors that block the Magi-1/E4 PDZ/PL interaction can restore tight junctions, polarity and growth control in breast cancer cells. The latter intervention can constitute a useful therapeutic strategy in treatments of breast cancer; and,
   g. In melanoma, the PDZ protein Syntenin/mda9 interacts with PL resulting in phosphorylation of focal adhesion kinase, c-Jun-NH2-kinase, and p38. The latter PDZ/PL interaction promotes metastasis that is linked to the levels of expression of Syntenin in a certain patient's cancer cells (Boukerche et al., 2005). Thus, using diagnostic assays to identify patients having melanoma cells with higher levels of Syntenin selects a population of patients who will benefit most from therapies with small molecule inhibitors of Syntenin-PDZ/PL interactions. The latter intervention constitutes an effective therapeutic strategy for limiting metastasis of the most aggressive and life threatening forms of melanoma;

2) Blocking PDZ/PL interactions in pain, the PDZ protein NHERF-1 interacts with PL in acid sensing ion channels (ASICs) involved in pain (Deval et al., 2005). Thus, small molecule inhibitors that block the NHERF-1/ASIC PDZ/PL interaction can reduce pain; and, 3) Blocking PDZ/PL interactions in stroke, the PDZ protein PSD95 interacts with PL in NMDA receptors involved in excitotoxic damage. Thus, small molecule inhibitors that block the PDZ/PL interaction of PSD95 with NMDA receptors can reduce ischemic damage in the acute phase of stroke, trauma and cardiovascular ischemia.

C. Exemplary Small Molecule Inhibitors

As discussed above, the general structure of the molecules of the present invention can be depicted as $P_0$-A-B-C-D-E. In the following pages, a number of putative structures for each of these positions is presented. These may be selected independently and combined however chemically feasible.

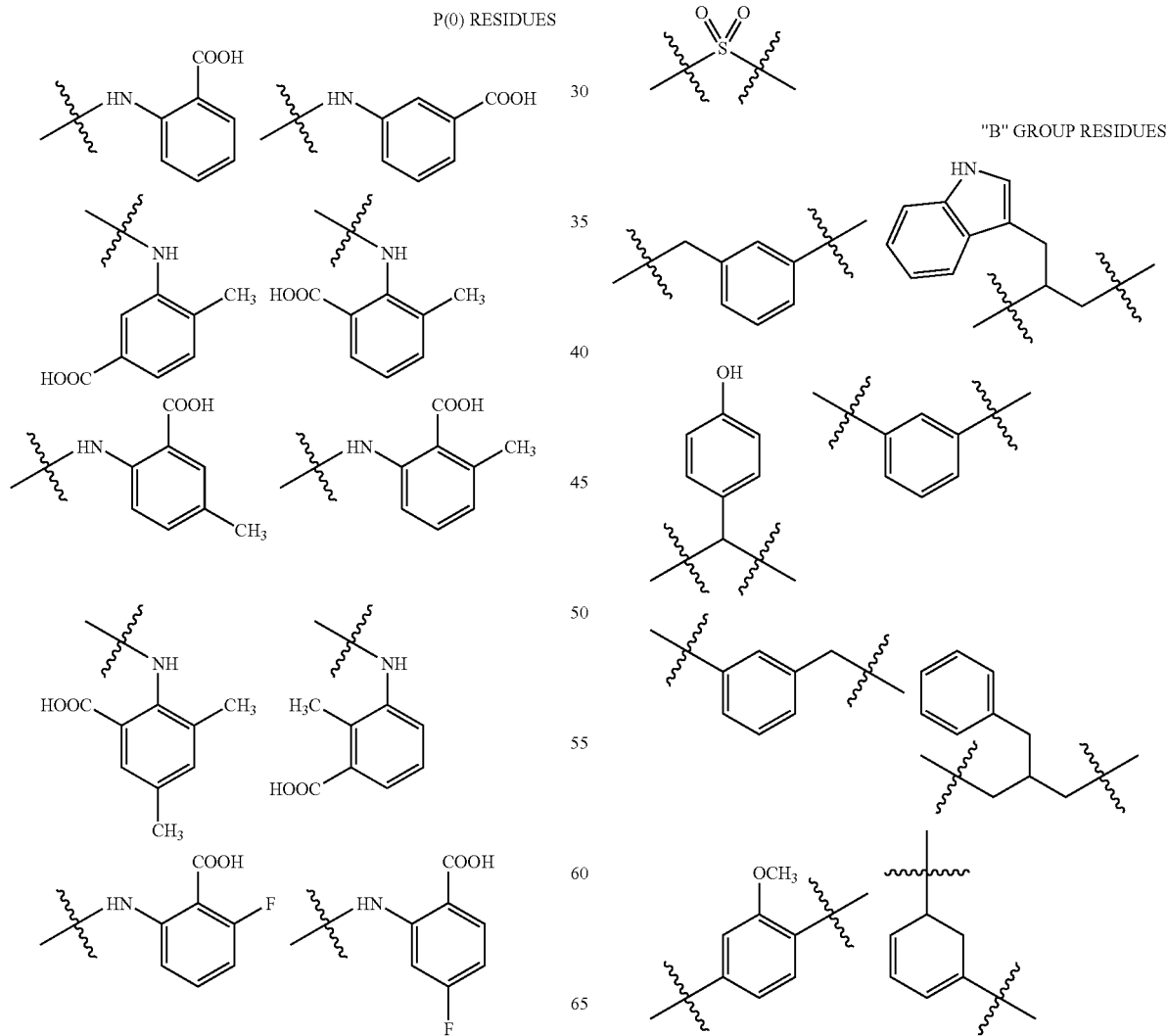

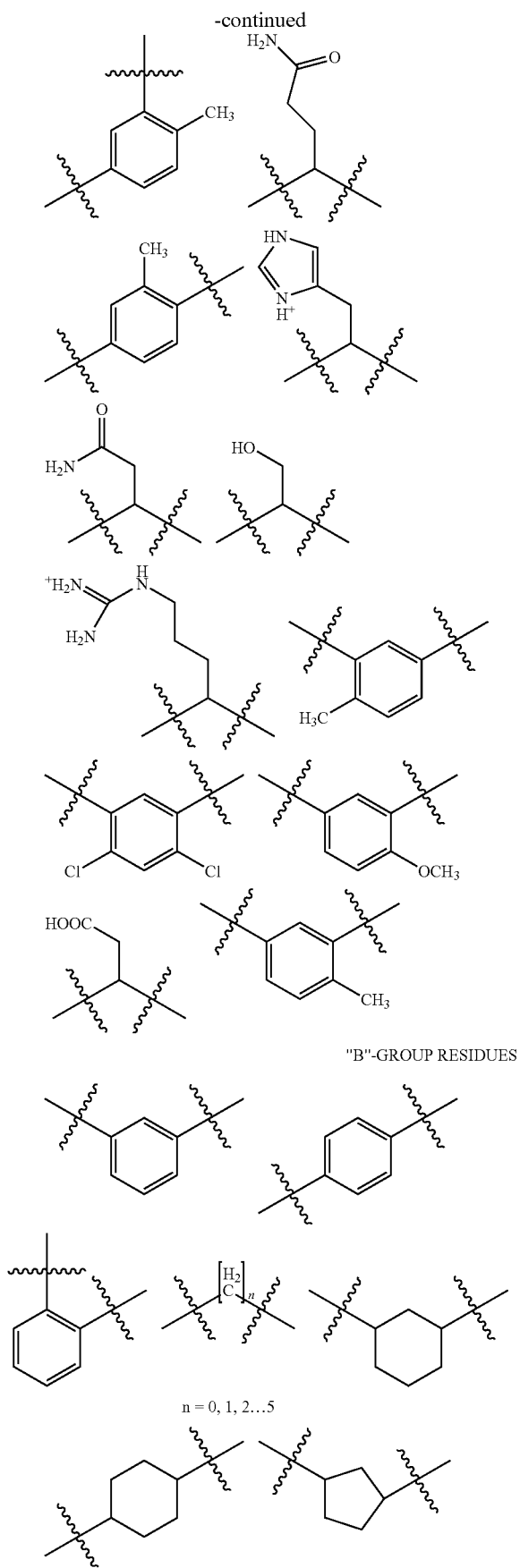
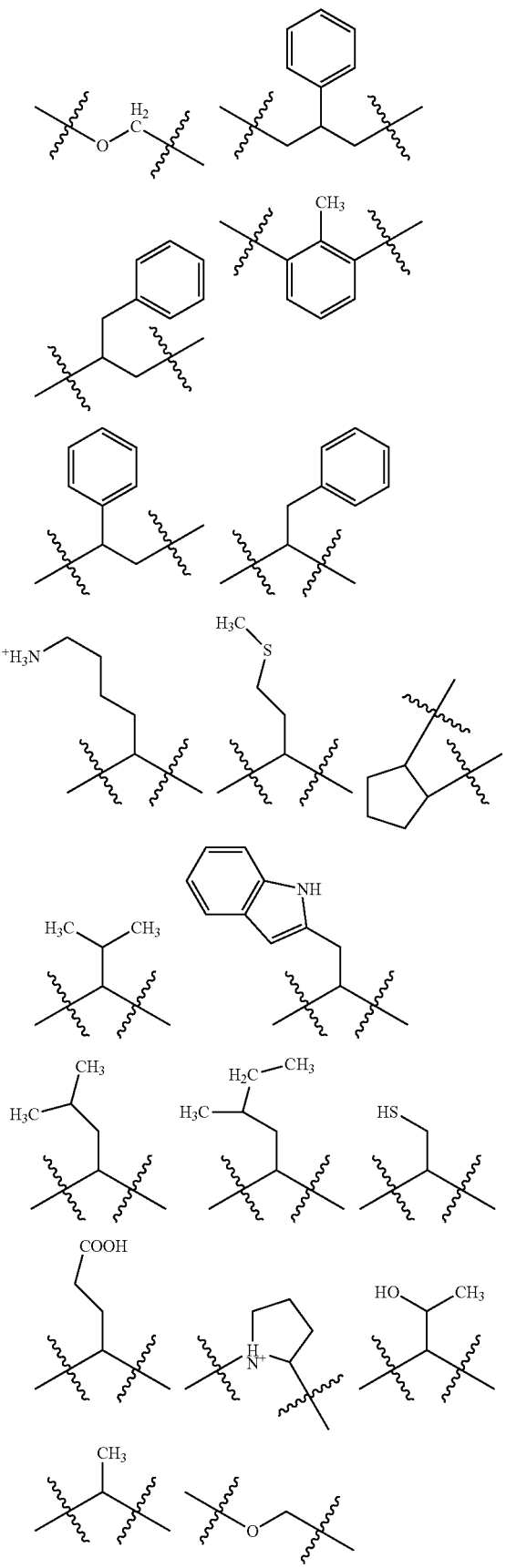
"B"-GROUP RESIDUES
n = 0, 1, 2...5

"C"-GROUP RESIDUES
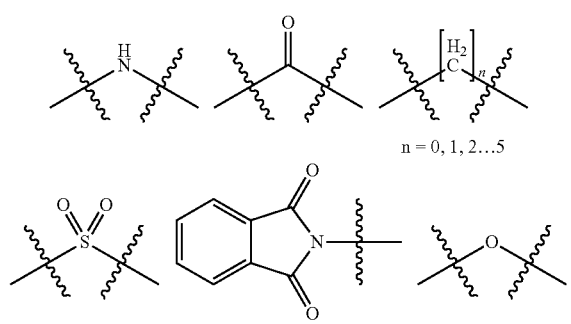
"D"-GROUP RESIDUES
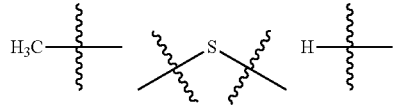
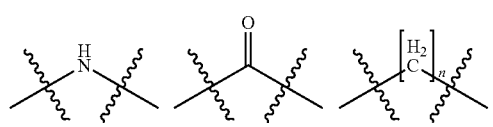
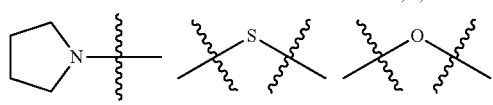
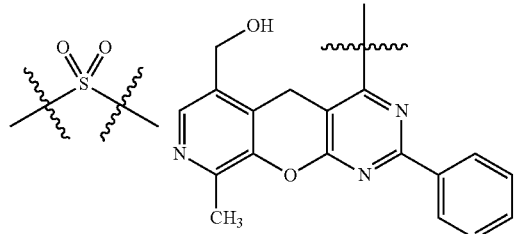
"E"-GROUP RESIDUES
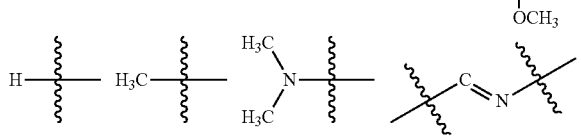
n = 1, 2...16
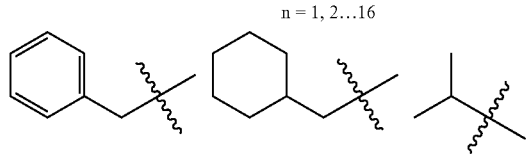
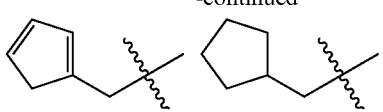
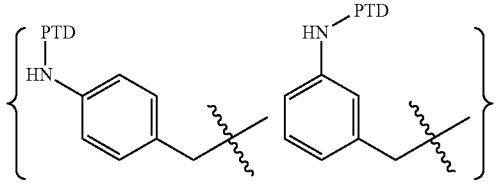
PTD-PROTEIN TRANSDUCTION DOMAIN: HIV-Tat, ANTENNAPEDIA
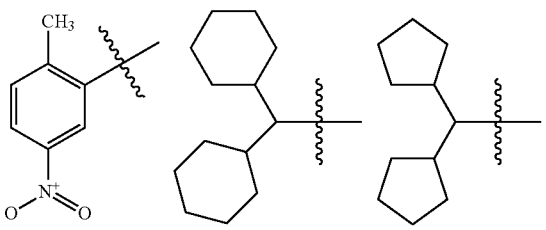
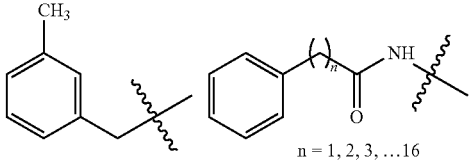
n = 1, 2, 3, ...16
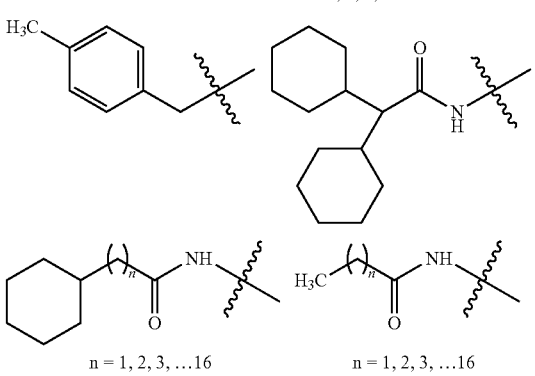
n = 1, 2, 3, ...16    n = 1, 2, 3, ...16
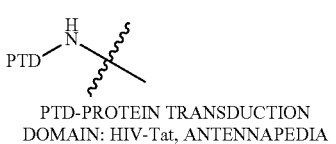
PTD-PROTEIN TRANSDUCTION DOMAIN: HIV-Tat, ANTENNAPEDIA
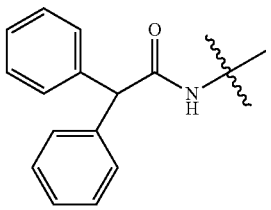
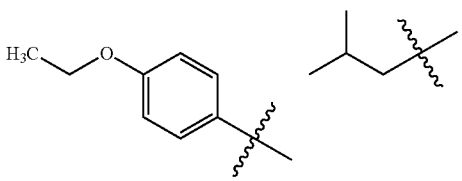

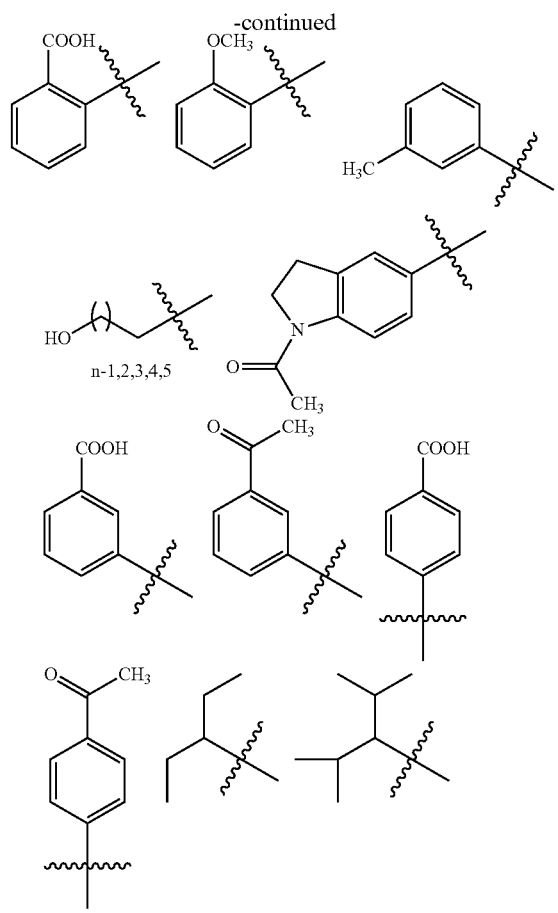

D. Membrane Translocation Sequences (MTS)

The instant therapeutic small molecule compounds may be further modified to make the compound more soluble or to facilitate its entry into a cell. For example, the compound may be modified by conjugation of fatty acyl groups or PEGylated at any available position; or alternatively, the compound may be conjugated to a peptide comprising a membrane translocation sequence/domain (MTS/MTD), also called an "internalization peptide," that facilitates translocation through the plasma membrane of a cell. MTSs can be derived from, e.g., a tat, Antennapedia or an N-terminal protein signal sequence peptide. MTS peptides are described in U. Langel, Ed. "Cell Penetrating Peptides," CRC Press, Boca Rotan, 2002, i.e., incorporated herein by reference in its entirety. Examples of small molecules conjugated with MTS peptides are illustrated in the Examples, below.

A number of peptide sequences have been described in the art as capable of facilitating the entry of a peptide linked to these sequences into a cell through the plasma membrane (Derossi et al., 1998). For the purpose of this invention, such peptides are collectively referred to as "transmembrane translocation sequence", which is used interchangeably with "cell penetrating peptides". Examples of the latter cell penetrating peptides include, but are not limited to the following: namely, tat derived from HIV (Vives et al., 1997; Nagahara et al., 1998), Antennapedia from *Drosophila* (Derossi et al., 1994), VP22 from Herpes Simplex virus (Elliot and D'Hare, 1997), complementarity-determining regions (CDR) 2 and 3 of anti-DNA antibodies (Avrameas et al., 1998), 70 KDa heat shock protein (Fujihara, 1999) and transportan (Pooga et al., 1998). In certain embodiments, a truncated HIV tat peptide may be employed.

Examples of linker technology for attaching the instant small molecule compound to an MTS peptide include: heterobifunctional cross-linking reagents, carbodiimide coupling reagents, glutaraldehyde, amide and ester linking reagents, thio linking reagents and the like.

The internalization peptide can comprise a variant of a standard tat sequence YGRKKRRQRRR. Although practice of the invention is not dependent on an understanding of mechanism, it is believed that both capacity to cross membranes and binding to N-type calcium channels are conferred by the unusually high occurrence of positively charged residues Y, R and K in the peptide. Variant internalization peptides for use in the invention should retain ability to facilitate uptake into cells but have reduced capacity to bind N-type calcium channels. Some suitable internalization peptides comprise or consist of an amino acid sequence XGRKKRRQRRR, in which X is an amino acid other than Y or nothing (in which case G is a free N-terminal residue). A preferred tat variant has the N-terminal Y residue substituted with F. Thus, a tat variant comprising or consisting of FGRKKRRQRRR is preferred. Another preferred variant tat internalization peptide consists of GRKKRRQRRR. If additional residues flanking XGRKKRRQRRR are present (beside the active peptide) the residues can be for example, natural amino acids flanking this segment from a tat protein, spacer or linker amino acids of a kind typically used to join two peptide domains, e.g., gly (ser)$_4$, T G E K P, GGR-RGGGS, or LRQRDGERP (see, e.g., Tang et al. (1996), J. Biol. Chem. 271, 15682-15686; Hennecke et al. (1998), Protein Eng. 11, 405-410)), or can be any other amino acids that do not detectably reduce capacity to confer uptake of the variant without the flanking residues and do not significantly increase inhibition of N-type calcium channels relative to the variant without the flanking residues. Preferably, the number of flanking amino acids other than an active peptide does not exceed ten on either side of XGRKKRRQRRR. Preferably, no flanking amino acids are present, and the internalization peptide is linked at its C-terminus directly to an active small molecule compound.

Other internalization peptides of the invention that can be used to allow uptake of any of the active small molecule inhibitors of the invention for inhibition of PSD-95 interactions without inhibiting N-type calcium channels include those presented in Table 3 below. It is recommended that these internalization peptides be screened to confirm desired uptake and lack of inhibition of N-type calcium channels, as described in the Examples of copending U.S. Provisional Application No. 60/904,507, filed Mar. 2, 2007, herein incorporated by reference in its entirety. The data presented in these examples demonstrate that mutation of the N-terminal tyrosine residue (Y) of Tat-NR2B9c to phenylalanine (F) is sufficient to abrogate inhibition of the N-type calcium channel without reducing the ability of the remainder of the peptide to localize to the site of action for this drug in the brain and reduce the damage following induced stroke in animals models of permanent ischemia. Further, the experiments demonstrate that Tat alone (YGRKKRRQRRR) is sufficient to induce the observed inhibition of the N-type calcium channel, and that different compounds added at the C-terminus have only a mild effect on the inhibition when attached to Tat. Thus, change or removal of the tyrosine at the N-terminus of the Tat sequence is likely to be important to reduction of binding. Mutation of basic amino acid residues near this tyrosine can also result in a reduction of binding to and inhibition of N-type calcium channels. The exemplary sequences in the table below are predicted herein to maintain transport capability without inhibiting N-type calcium channels and thus allow a greater therapeutic index for the treatment of stroke or neurotrauma.

TABLE 3

X-FGRKKRRQRRRKLSSIESDV (F-TatNR2B9c)
X-GKKKKKQKKKKLSSIESDV
X-RKKRRQRRRKLSSIESDV
X-GAKKRRQRRRKLSSIESDV
X-AKKRRQRRRKLSSIESDV
X-GRKARRQRRRKLSSIESDV
X-RKARRQRRRKLSSIESDV
X-GRKKARQRRRKLSSIESDV
X-RKKARQRRRKLSSIESDV
X-GRKKRRQARRKLSSIESDV
X-RKKRRQARRKLSSIESDV
X-GRKKRRQRARKLSSIESDV
X-RKKRRQRARKLSSIESDV
X-RRPRRPRRPRRKLSSIESDV
X-RRARRARRARRKLSSIESDV
X-RRRARRRARRKLSSIESDV
X-RRRPRRRPRRKLSSIESDV
X-RRPRRPRRKLSSIESDV
X-RRARRARRKLSSIESDV

X can represent a free amino terminus, a biotin molecule or other capping moiety including, but not limited to, H, acetyl, benzoyl, alkyl group (aliphatic), pyroglutamate, alkyl group with cycloalkyl group at the end, biotin with alkyl spacer, (5,6)-FAM. Chemical coupling of the capping group to the N-terminal peptide can be through an amide chemistry, sulphamide chemistry, sulphone chemistry, alkylation chemistry. In addition, X can also be an amino acid other than tyrosine.

VI. Pharmaceutical Formulations

Pharmaceutical compositions of the present invention comprise an effective amount of one or more PDZ/PL interaction modulators, optionally with an additional agent, dissolved or dispersed in a pharmaceutically acceptable carrier. The phrases "pharmaceutical" or "pharmacologically acceptable" refer to molecular entities and compositions that do not produce an adverse, allergic or other untoward reaction when administered to an animal, such as, for example, a human, as appropriate. The preparation of an pharmaceutical composition that contains at least one PDZ/PL modulators, and optionally additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 1990, incorporated herein by reference). Except insofar as any conventional carrier is incompatible with the active ingredient, its use in the therapeutic or pharmaceutical compositions is contemplated.

The PDZ/PL interaction modulator may be formulated with different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference). In particular embodiments, prolonged absorption of an injectable composition can be brought about by the use in the compositions of agents delaying absorption, such as, for example, aluminum monostearate, gelatin or combinations thereof.

The actual dosage amount of a composition of the present invention administered to an animal patient can be determined by physical and physiological factors such as body weight, severity of condition, the type of disease being treated, previous or concurrent therapeutic interventions, idiopathy of the patient and on the manner and/or route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

The compounds are used in an amount effective to achieve the intended purpose (e.g., reduction of damage effect of the damaging stroke and related conditions). A therapeutically effective amount means an amount of compound or compounds sufficient to significantly reduce the damage resulting from stroke in a population of patients (or animal models) treated with the compounds of the invention relative to the damage in a control population of stroke patients (or animal models) not treated with the compounds of the invention. The amount is also considered therapeutically effective if an individual treated patient achieves an outcome more favorable than the mean outcome (determined by infarction volume or disability index) in a control population of comparable patients not treated by methods of the invention. The amount is also considered therapeutically effective if an individual treated patient shows a disability of two or less on the Rankin scale and 75 or more on the Barthel scale. A dosage is also considered therapeutically effective if a population of treated patients shows a significantly improved (i.e., less disability) distribution of scores on a disability scale than a comparable untreated population, see Lees et al., N Engl J Med 2006; 354:588-600. A therapeutically effective regime means a combination of a therapeutically effective dose and a frequency of administration needed to achieve the intended purpose as described above. Usually a single administration is sufficient.

Preferred dosage ranges include 0.001 to 20 µmol of compound per kg patient body weight. In other instances, the dosages range is from 0.005 to 5 µmol compound per kg patient body weight, optionally 0.01-5 µmol of compound per kg patient body weight. In some methods, 0.3 to 3 µmol compound per kg patient body weight are administered. In some methods, 0.1-1 µmol compound per kg patient body weight is administered, more preferably about 0.5 µmol compound per kg patient body weight. Dosage per kg body weight can be converted from rats to humans by dividing by 6.2 to compensate for different surface area to mass ratios. Dosages can be converted from units of moles to grams by multiplying by the molar weight of a compound. Suitable dosages of compounds for use in humans can include 0.005 to 10 mg/kg patient body weight, or more preferably 0.02 to 5 mg/kg patient body weight or 0.1 to 1 mg/kg, or 0.2 to 0.9 mg/kg. In absolute weight for a 75 kg patient, these dosages translate to 0.075-375 mg, 0.375 to 75 mg or 7.5 mg to 75 mg or 12.5 to 67 mg. Rounded to encompass variations in e.g., patient weight, the dosage is usually within 0.5 to 500 mg, preferably 1 to 100 mg, 0.5 to 50 mg, or 1-20 mg. The compounds are preferably administered within 24 hours, more preferably within 6 hours, and most preferably within 3 hours, after initiation of stroke.

A therapeutically effective dose of the present compounds can provide therapeutic benefit without causing substantial toxicity. Toxicity of the compounds can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds exhibiting high therapeutic indices are preferred (see, e.g., Fingl et al., 1975, In: The Pharmacological Basis of Therapeutics, Ch. 1, p. 1).

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The PDZ/PL modulator may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the PDZ/PL modulator is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof, a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

VII. Therapies

A. Inflammatory and Neurodegenerative Diseases
i. Monotherapy

Compounds of the present invention may be useful in treatment strategies designed to ameliorate one or more symptoms of disease in patients with cancer, pain, inflammation or neurological disorders, including clinical sequelae resulting therefrom.

In certain embodiments, compounds and methods of the present invention are useful in therapeutic strategies for treating a subject at risk of, or having undergone, stroke. Stroke is a leading cause of death and disability in industrialized nations. Nearly 500,000 people in the United States suffer from stroke syndromes annually, at a cost of $23 billion. Strokes are caused primarily by an abrupt interruption of blood flow to a portion of the brain, due to arterial blockage. A less common cause of stroke is haemorrhaging due to a ruptured cerebral aneurysm. Accordingly, the instant methods and composition are also useful in strategies for treatments of stroke resulting from ischemic infarction, embolism and hemorrhage, e.g., hypotensive hemorrhage. Since strokes affect only one side of the brain, symptoms typically involve only one side of the body. Common symptoms include muscle weakness, numbness, reduction in sensory or vibratory sensation, decreased reflexes, paralysis, vision problems, loss of balance, loss of coordination, and speech impairment.

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a patient as follows.

TABLE 4

0 No symptoms at all
1 No significant disability despite symptoms; able to carry out all usual duties and activities.
2 Slight disability; unable to carry out all previous activities but able to look after own affairs without assistance.
3 Moderate disability requiring some help, but able to walk without assistance
4 Moderate to severe disability; unable to walk without assistance and unable to attend to own bodily needs without assistance.
5 Severe disability; bedridden, incontinent, and requiring constant nursing care and attention.

The Barthel Index is based on a series of questions about the patient's ability to carry out 10 basic activities of daily living resulting in a score between 0 and 100, a lower score indicating more disability (Mahoney et al., Maryland State Medical Journal 14:56-61 (1965)).

Alternatively stroke severity/outcomes can be measured using the NIH stroke scale, available at world wide web ninds.nih.gov/doctors/NIH_Stroke_Scale_Booklet.pdf. The scale is based on the ability of a patient to carry out 11 groups of functions that include assessments of the patient's level of consciousness, motor, sensory and language functions.

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel ruptures. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

Several other neurological conditions can also result in neurological death through NDMAR-mediated excitotoxicity. These conditions include epilepsy, hypoxia, traumatic injury to the CNS not associated with stroke such as traumatic brain injury and spinal cord injury, Alzheimer's disease and Parkinson's disease.

Certain conditions may exacerbate stroke: A subset of stroke patients have exacerbating fever and/or hyperglycemia, which are comorbid conditions, that in the absence of treatment by the present methods predispose patients to a poorer outcome than is the case for all stroke patients, particularly stroke patients lacking such an exacerbating comorbidity. Details are provided in U.S. Provisional App. No. 60/833,572, which is herein incorporated by reference in its entirety.

Compounds of the present invention may be used to treat and/or reduce these and other stroke-related symptoms.

Treatment is usually initiated as soon as possible after initiation of the stroke. Occasionally, treatment can be initiated at or before onset of stroke in patients known to be at high risk. Risk factors include hypertension, diabetes, family history, smoking, previous stroke, and undergoing surgery. Usually, treatment is first administered within one to 24 hours after initiation of stroke. Often a single dose of a compound of the invention is sufficient. However, multiple doses can also be administered at intervals of 6-24 hr or greater.

The response of the patient to the administration of a compound of the invention can be monitored by determining infarction volume before and at various times after treatment. Early ischemia is detectable using MRI diffusion imaging. Combinations of MRI protocols, including perfusion imaging, can be used to determine tissue at risk and predict infarction volume. The methods preferably achieve a reduction in infarction volume of at least 10, 15, 20, 25, 30, 35, 40, or 50% relative to the mean infarction volume in a population of comparable patients not receiving treatment by the methods of the invention. The response of the patient can also be measured from a disability index determined one day to one week after initiating treatment. The patient preferably shows an improvement (i.e., less disability) in disability index of at least 4, 10, 15, 20, 25, 30, 35, 40, or 50% relative to the mean disability index in a population of comparable patients not receiving treatment by the methods of the invention The patient preferably scores a zero or one on the Rankin stroke index or over 75 on the Barthel index.

In certain embodiments, the subject compounds may be administered to a subject suffering from pain and/or inflammation (e.g., arthritis, retinopathy, SLE, psoriasis, Bullous pemphigoid, shingles, or a similar condition). In other embodiments, the instant compounds and methods are useful in therapeutic strategies for treating a subject at risk of, or having undergone, microvascular insufficiency, hypoxia, atherosclerosis or another acute or chronic cardiovascular and neurological ischemic events. In other particular embodiments, the subject compounds may be employed in therapeutic strategies designed to limit neuronal damage in patients with mild to severe traumatic brain injury, including diffuse axonal injury, hypoxic-ischemic encephalopathy and other forms of craniocerebral trauma. Further, the instant compounds and methods may be used to treat complications resulting from infections of the nervous system, such as bacterial or viral meningitis. Moreover, the instant compounds and methods may also be useful in treatment strategies for neurodegenerative diseases including Alzheimer's disease, Lewy Body dementia, Parkinson's disease (PD), Huntington's disease (HD), multiple sclerosis, motor neuron disease, muscular dystrophy, peripheral neuropathies, metabolic disorders of the nervous system including glycogen storage diseases, and other conditions where neurons are damaged or destroyed.

ii. Combination Therapies

In particular embodiments, where treatments are directed toward alleviating one or more symptoms of inflammation, the subject compounds may be co-administered in conjunction with an inhibitor of prostaglandin synthesis by COX (which may be a non-specific or specific COX). Such a compound may be a non-steroidal anti-inflammatory drug (NSAID) including, for example, aspirin, indomethacin (Indocin®), ibuprofen (Motrin®), naproxen (Naprosyn®), piroxicam (Feldene®), nabumetone (Relafen™), rofecoxib (Vioxx®), celecoxib (Celebrex™) or valdecoxib (Bextra™).

In other combinations, Betaseron®, Avonex®, Copaxone®, Novantrone®, and Rebif® may be useful in combination with the instant small molecule compounds, for example, in treatments for demyelinating disease such as multiple sclerosis; Aricept® (donepezil) and Exelon® (rivastigmine) which are reversible acetylcholinesterase inhibitors indicated in treatments of mild to moderate dementia of the Alzheimer's type may be also be used in combination therapies with the instant small molecule compounds; and, and Rilutek®, Lioresol®, Zanaflex®, NSAIDs and Ultram®, which are currently used in patients with amyotrophic lateral sclerosis, may also be useful in combined therapies. Parkinson's combination therapies may involve the instant small molecule compound and anti-cholinergic (anti-muscarinic) drugs, COMT inhibitors, L-Dopa, dopamine receptor agonists, and/or MAO-B inhibitors.

B. Cancer i. Monotherapy

As illustrated above, compositions of the present invention will also be useful in treating cancers, including primary, metastic, drug resistant and recurrent cancers. In such embodiments, the subject compositions may be administered to a subject suffering a hyperproliferative disease such as cancer or, in other embodiments, a subject at an increased relative risk for developing cancer.

A hyperproliferative disease is a disease associated with the abnormal growth or multiplication of cells. Exemplary hyperproliferative sites include pre-malignant lesions, benign tumors, and cancers. The composition and methods of the present invention may be used in therapeutic strategies designed to ameliorate one or more symptoms associated with solid cancers, including, e.g., cancer of the brain, head & neck, esophagus, tracheus, lung, liver, stomach, colon, pancreas, breast, cervix, uterus, bladder, prostate, testicules, skin or rectum. The instant compounds and methods may also be used in therapies of lymphomas or leukemias.

Local, regional (together loco-regional) or systemic delivery of the instant compositions to patients is contemplated. the instant therapeutic approaches constitute intervention strategies that will provide clinical benefit by ameliorating one or more symptoms of disease, defined broadly as any of the following: reducing tumor-associated pain, reducing primary tumor size, reducing occurrence or size of metastasis, reducing or stopping tumor growth, inducing remission, increasing the duration before recurrence, inhibiting tumor cell division, killing a tumor cell, inducing apoptosis in a tumor cell, reducing or eliminating tumor recurrence, and/or increasing patient survival.

A cancer recurrence may be defined as the reappearance or rediagnosis of a patent as having any cancer following one or more of surgery, radiotherapy or chemotherapy. The patient need not have been reported as disease free, but merely that the patient has exhibited renewed cancer growth following some degree of clinical response by the first therapy. The clinical response may be, but is not limited to, stable disease, tumor regression, tumor necrosis, or absence of demonstrable cancer.

ii. Combination Therapies

In accordance with the present invention, additional therapies may be applied with further benefit to the patients. Such therapies include radiation, chemotherapy, surgery, cytokines, toxins, drugs, dietary, or gene therapy. Examples are discussed (above), and below.

To kill cancer cells, slow their growth, or to achieve any of the clinical endpoints discussed above, one may contact the cancer cell or tumor with compositions of the present invention in combination with a second anti-cancer therapy. These two modalities are be provided in a combined amount effective to kill or inhibit proliferation of the cancer cell, or to achieve the desired clinical endpoint, including increasing patient survival. This process may involve contacting the cancer cell or tumor with both modalities at the same time. This may be achieved by contacting cancer cell or tumor with a single composition or pharmacological formulation that includes both agents, or by contacting the cancer cell or tumor with two distinct compositions or formulations, at the same time, wherein one composition includes the primary therapy, and the other includes the second therapy.

Alternatively, the primary therapy may precede or follow the second therapy by intervals ranging from minutes to weeks. In embodiments where the two modalities are applied separately to the cancer cell or tumor, one would generally ensure that a significant period of time did not expire between the time of each delivery, such that both would still be able to exert an advantageously combined effect on the cancer cell or tumor. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6, or 7) to several weeks (1, 2, 3, 4, 5, 6, 7 or 8) lapse between the respective administrations.

It is also conceivable that more than one administration of each modality will be desired. Various combinations may be employed, where the primary therapy is "A" and the second therapy is "B":

| | | | | | | | |
|---|---|---|---|---|---|---|---|
| A/B/A | B/A/B | A/B/A | A/A/B | A/B/B | B/A/A | B/B/B/A | B/A/B/B |
| B/B/A/B | A/A/B/B | A/B/A/B | A/B/B/A | | B/B/A/A | B/A/B/A | |
| B/A/A/B | A/A/A/B | B/A/A/A | A/B/A/A | | A/A/B/A | A/B/B/B | |

The terms "contacted" and "exposed," when applied to a cancer cell or tumor, are used herein to describe the process by which an agent or agents is/are delivered to a cancer cell or tumor or are placed in direct juxtaposition thereto.

a. Subsequent Surgery

Approximately 60% of persons with cancer will undergo surgery of some type, which includes preventative, diagnostic or staging, curative and palliative surgery. In particular, patients with unresectable tumors may be treated according to the present invention. As a consequence, the tumor may reduce in size, or the tumor vasculature may change such that the tumor becomes resectable. If so, standard surgical resection may be permitted. Another particular mode of administration that can be used in conjunction with surgery is treatment of an operative tumor bed, created by surgery. Thus, in either the primary treatment, or in a subsequent treatment, one may perfuse the resected tumor bed with the composition during surgery, and following surgery, optionally by inserting a catheter into the surgery site.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

As stated above, upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

b. Gene Therapy

In another embodiment, the secondary treatment is a gene therapy in which a therapeutic gene is administered to the subject. A variety of molecules are encompassed within this embodiment, including tumor suppressors, cell cycle regulators, pro-apoptotic genes, cytokines, toxins, anti-angiogenic factors, and molecules than inhibit oncogenes, pro-angiogenic factors and growth factors.

c. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

d. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively).

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Stereotactic radiotherapy is used to treat brain tumours. This technique directs the radiotherapy from many different angles so that the dose going to the tumour is very high and the dose affecting surrounding healthy tissue is very low. Before treatment, several scans are analysed by computers to ensure that the radiotherapy is precisely targeted, and the patient's head is held still in a specially made frame while receiving radiotherapy. Several doses are given.

Stereotactic radio-surgery (gamma knife) for brain tumors does not use a knife, but very precisely targeted beams of gamma radiotherapy from hundreds of different angles. Only one session of radiotherapy, taking about four to five hours, is needed. For this treatment you will have a specially made metal frame attached to your head. Then several scans and x-rays are carried out to find the precise area where the treatment is needed. During the radiotherapy, the patient lies with their head in a large helmet, which has hundreds of holes in it to allow the radiotherapy beams through.

Scientist also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

e. Other Therapies

Immunotherapy. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Tumor Necrosis Factor is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

Hormonal Therapy.

The use of sex hormones according to the methods described herein in the treatment of cancer. While the methods described herein are not limited to the treatment of a specific cancer, this use of hormones has benefits with respect to cancers of the breast, prostate, and endometrial (lining of the uterus). Examples of these hormones are estrogens, antiestrogens, progesterones, and androgens.

Corticosteroid hormones are useful in treating some types of cancer (lymphoma, leukemias, and multiple myeloma). Corticosteroid hormones can increase the effectiveness of other chemotherapy agents, and consequently, they are frequently used in combination treatments. Prednisone and dexamethasone are examples of corticosteroid hormones.

C. Immunodulation

PDZ modulators may also find use in the treatment of immune-based diseases. Such diseases include those with abnormal immune activation, such as autoimmune SLE rheumatoid arthritis, Bullous pemphigoid, Type-I diabetes, and the like; while others may involve those characterized by insufficient immune function. The former maybe treated in combination using immunosuppressive agents (FK506, cyclosporin, tacrolimus, cyclophosphamide, methotrexate, cotrimoxazole and MMF) and the instant small molecule modulators of PDZ:PL interactions.

D. Mental Illness

Other diseases that may be subject to treatment with compositions of the present invention include psychiatric disorders such as attention deficit hyperactive disorder, depression, agoraphobia, bulimia, anorexia, bipolar disorder, anxiety disorder, autism, dementia, dissociative disorder, hypochondriasis, impulse control disorder, kleptomania, mood disorder, multiple personality disorder, chronic fatigue syndrome, insomnia, narcolepsy, schizophrenia, substance abuse, post-traumatic stress disorder, obsessive-compulsive disorder, and manic depression.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Molecular Modeling Protocol: In Silico Screening

Molecular modeling was performed using the Accelrys molecular modeling software package. Briefly, the structures of four different PDZ proteins, i.e., human DVL1, PSD95 d1, PSD95 d2, and PSD95 d3, were used to construct approximated/optimized/chimeric molecular coordinates and these coordinates were then, in turn, used to construct in silico PDZ domain models for docking different small molecule compounds. The molecular coordinates for human DVL1 were partially derived from homology modeling based on a *Xenopus* DVL2 (#1L60.pdb) crystal structure. Molecular coordinates were also adjusted to consider experimental and theoretical NMR-defined structures for PSD95 d1, PSD95 d2, and PSD95 d3. In silico docking of small molecules at the PDZ's was performed with the Structure Based Focusing (SBF) module of Cerius2 (Accelrys, San Diego, Calif.) as well as the Catalyst 4.9 modeling program. The molecular modeling procedure may be broken up into several steps:

1) Preparation of an excluded volume surface to approximate the shape of the PDZ binding groove;

2) Definition of pharmacophore groups in the PDZ binding groove. In essence, a set of pharmacophore filters were sequentially enforced, i.e., requiring certain specific small molecule/PDZ interactions with amino acid residues in the groove, e.g., including hydrogen bond donors, hydrogen bond acceptors and hydrophobic interactions. In multiple rounds of modeling, test compounds were accepted as "hits" if the molecules did not clash with the excluded volume of the PDZ groove and they also fulfilled the interactions required by the enforced pharmacophore filters. In all cases, two mandatory requirements were enforced: namely, for all molecules (a) they must interact with the position zero pocket (P0) of the PDZ via a hydrophobic interaction, and (b) they must have a carboxylate functional group in proximity of the "GLGF" loop of the PDZ groove;

3) The filter composed of parts-1 (excluded volume) and -2 (pharmacophore groups) was imported into Catalyst 4.9-4.10 and used to search chemical databases containing multiple conformations for each molecule; and, 4) From approximately 650,000 test compounds (ChemDiv, San Diego, Calif.; Blanca Pharmaceutical, Mountain View, Calif.) subject to molecular modeling just 184 small molecule compounds were selected from the "possible hits lists" for experimental testing, i.e., as disclosed in EXAMPLE 2, below. Briefly, each of the "possible hits" were each tested for competitive inhibition of PDZ ligand binding at six different PDZ domains, i.e., competition in each of six different PDZ/PDZ ligand assays involving PSD95 d1, PSD95 d2, PSD95 d3, Magi1 d1, Tip1 and Shank1.

Example 2

Matrix Modified G-Assay

Small Molecule Competition Assay.

The reagents, supplies and protocol are as follows:

Reagents and Supplies:
(1) Nunc Maxisorp 96 well Immuno-plates
(2) PBS pH 7.4 (phosphate buffered saline, 8 g NaCl, 0.29 g KCl, 1.44 g $Na_2HPO_4$, 0.24 g
(3) $KH_2PO_4$, add $H_2O$ to 1 L and pH 7.4; 0.2µ filter)
(4) Assay Buffer: 2% BSA in PBS (20 g of BSA per liter PBS), ICN Biomedicals
(5) Goat anti-GST polyclonal antibody, stock 5 mg/ml, stored at 4° C., (Amersham Pharmacia); Diluted 1:1000 in PBS to a final concentration 5 µg/ml
(6) HRP-Streptavidin, 2.5 mg/2 ml stock stored @4° C., Zymed,—dilute 1:2000 into Assay buffer, final [0.5 µg/ml]
(7) Biotinylated peptides (from Anaspec, stored in −20° C. freezer)
(8) GST-PRISM proteins (stock stored @−80° C., after $1^{st}$ thaw store in −10° C. freezer)
(9) TMB (3,3',5,5', teramethylbensidine), ready to use
(10) 0.18M $H_2SO_4$
(11) 12-w multichannel pipettor
(12) 200 µl LTS tips
(13) 50 ml reagent reservoirs
(14) 50 polypropylene conical tubes
(15) 15 ml polypropylene round-bottom tubes
(16) 1.5 ml microtubes
(17) Molecular Devices microplate reader (450 nm filters)
(18) SoftMax Pro software
(19) Assay buffer (1×PBS, 0.01% Triton X-100)

Protocol. The wells of eighteen to twenty 96-well plates were coated with 100 µl of 5 µg/ml anti-GST antibody (in each well), and left overnight at 4° C. The plates were then emptied by inverting and tapped dry on paper towels. 200 µl of blocking buffer (1×PBS/2% BSA) was added to each well and the plates were left for 1-2 hrs at room temperature. The plates were then washed using the automatic plate washer (3× with room temperature 1×PBS), insuring that the plates did not dry out. GST-PDZ fusion proteins were diluted to a final concentration of 5 µg/ml in 1×PBS/2% BSA and 50 µl was added to each well. After incubating for 1-2 hours at 4° C. excess unbound fusion protein was removed by washing, i.e., using the automatic plate washer (3× with room temperature 1×PBS).

PDZ ligand peptides, small molecule test compounds, and HRP were prepared in Assay Buffer as follows:

Biotinylated PDZ ligand synthetic peptides were prepared in one-quarter final volume, i.e., at 4× final concentration;

Steptavidin-HRP conjugate (Zymed) was diluted (1:500) in one-quarter final volume, i.e., at 4× final concentration;

Biotinylated peptides and Streptavidin-HRP were then mixed together, and incubated for 20 min at room temperature to form a signal generating peptide ligand complex;

While the peptide/HRP mix was incubating, test compound dilutions were prepared in half the final volume, i.e., at 2× final concentration; and, Immediately before adding the final peptide ligand complex mixture to the plate, the drug titration was added to give a mixture with 1× concentrations and the final correct total volume.

The signal generating peptide ligand/test compound mixtures were then added to each well of the plates to give 50 µl per well and the time of each addition was recorded. The plates were then incubated at room temperature, after the last peptide had been added, for exactly 30 min. After incubation, the plates were washed using the automatic plate washer (7× with room temperature 1×PBS). To detect the signal generating peptide ligand TMB substrate (for HRP) was added to each well of the plates at 100 µl per well and the time of TMB addition was recorded. The plates were then incubated in the dark at room temperature for a maximum of 30 min. The calorimetric reaction was then stopped using 100 µl of 0.18M $H_2SO_4$ 30 minutes after adding TMB. The signal in each well of the plates were then determined by measuring the optical density at 450 nm.

PDZ Ligand Peptides.

The description for FIG. 1 (below) shows the six PDZ proteins and biotinylated-PL pairs used in competition screening assays. The chemical structures of illustrative small molecule competitor compounds are set forth in FIG. 2A.

Illustrative Results in Screening.

Small molecules were screened for their ability to compete with peptides for PDZ binding in the competitive binding assay, supra. Illustrative results are presented in FIG. 1, i.e., the $OD_{450}$ values of the eight selected small molecule inhibitors shown alongside the $OD_{450}$ values of the corresponding eight DMSO controls. The particular PDZ/PL interactions illustrated in FIG. 1 were as follows:

(1) Control: PL peptide 1857 (GRWTGRSMSSWKPTR-RETEV)+PDZ protein Magi1 d1;
(2) Test: PL peptide 1857 (GRWTGRSMSSWKPTR-RETEV)+PDZ protein Magi1 d1+compound 8009-5039;
(3) Control: PL peptide AA56 (QISPGGLEPPSEKH-FRETEV)+PDZ protein Tip 1;
(4) Test: PL peptide AA56 (QISPGGLEPPSEKH-FRETEV)+PDZ protein Tip 1+compound 3289-2331;
(5) Control: PL peptide 1965 (YGRKKRRQRRRYI-PEAQTRL)+Shank 1;
(6) Test: PL peptide 1965 (YGRKKRRQRRRYI-PEAQTRL)+Shank 1+competitor 0620-005;
(7) Control: PL peptide 1916 (YGRKKRRQRRRT-KNYKQTSV)+PDZ protein PSD95-d3;
(8) Test: PL peptide 1916 (YGRKKRRQRRRT-KNYKQTSV)+PDZ protein PSD95-d3+compound C450-0454;
(9) Control: PL peptide 1857 (GRWTGRSMSSWKPTR-RETEV)+PDZ protein Magi1-d1;
(10) Test: PL peptide 1857 (GRWTGRSMSSWKPTR-RETEV)+PDZ protein Magi1-d1+compound 3019-0348;
(11) Control: PL peptide 1857 (GRWTGRSMSSWKPTR-RETEV)+PDZ protein Magi1-d1;
(12) Test: PL peptide 1857 (GRWTGRSMSSWKPTR-RETEV)+PDZ protein Magi1 d1+compound 3558-0042;
(13) Control: PL peptide 1857 (GRWTGRSMSSWKPTR-RETEV)+PDZ protein Magi1-d1;
(14) Test: PL peptide 1857 (GRWTGRSMSSWKPTR-RETEV)+PDZ protein Magi1-d1+compound MC 247808;
(15) Control: PL peptide 1916 (YGRKKRRQRRRT-KNYKQTSV)+PDZ protein PSD95-d3; and,
(16) Test: PL peptide 1916 (YGRKKRRQRRRT-KNYKQTSV)+PDZ protein PSD95 d3+compound E544-0129.

The numbers in parenthesis (above) correspond to the numbers in parenthesis below the bar graphs in FIG. 1.

Example 3

Small Molecules can Compete Binding of PDZ Ligands at PDZ Domains

Songyang et al. (1997) screened peptide libraries to evaluate binding of peptide PDZ ligands to LIN-2, p55 and Tiam-1 PDZ proteins with the finding that the carboxyl-terminal 3 to 7 amino acid residues contributed to binding. Subsequent confusion in the literature was summarized recently as "A compendium of information regarding PDZ complexes demonstrates that dissimilar C-terminal peptides bind to the same PDZ domain, and different PDZ domains can bind the same peptides." Niv et al. (2005). In general, molecular interactions involved in docking large peptides at PDZ domains have not been particularly helpful in designing small molecule inhibitors of PDZ/PL interactions.

The relative binding affinities of the compounds in FIG. 2A, and other, small molecule inhibitors were determined by titrating the compounds in the same competitive binding assay.

Illustrative $IC_{50}$ values (µM) for the small molecule compounds of FIG. 2A, i.e., as determined in titration studies against six different PDZ proteins are shown in TABLE 1 (below) and illustrative titration binding curves are shown in FIG. 2B as follows:

Panel 1) Titrations for Compound #3289-2331;
Panel 2) Titrations for Compound #0620-0057;
Panel 3) Titrations for Compound #C450-0454;
Panel 4) Titrations for Compound #3558-0042;
Panel 5) Titrations for Compound # MC 247808; and,
Panel 6) Titrations for Compound # E544-0129.

TABLE 1

Relative binding affinities of small molecules as determined by titration analysis

| Cmpd. No. | Magil d1 | PSD95 d1 | PSD95 d2 | PSD95 d3 | Shank 1 | Tip1 |
|---|---|---|---|---|---|---|
| 8009-5039 | >250 | >250 | >250 | >250 | >250 | >250 |
| 3289-2331 | 130.33 | >250 | >250 | >250 | >250 | >250 |
| 0620-0057 | 236.97 | 2.7 | 14.88 | 8.19 | 48.61 | >250 |
| C450-0454 | >250 | 206.07 | >250 | >250 | >250 | >250 |
| 3019-0348 | >250 | >250 | >250 | >250 | >250 | >250 |
| 3558-0042 | >250 | >250 | >250 | >250 | >250 | >250 |
| MC 247808 | >250 | >250 | 220.8 | >250 | >250 | >250 |
| E544-0129 | 60.76 | 2.5 | 4.98 | 3.47 | 7.59 | >250 |

Example 4

Membrane Translocation Sequences

A membrane translocation sequence/domain (MTD) is coupled to a fragment of the small molecule, preferably but not exclusively at fragment E. If the small molecule terminates at fragments D, C, or B, then an MTD may be covalently attached to fragments D, C, or B, respectively. The MTD may be coupled to the small molecule via an amide linkage, an ester linkage, a thioamide linkage or other form of covalent attachment. However, the MTD may not be attached to the P(0) carboxylate or phenyl since these functional groups are important for binding to the PDZ. FIGS. 3A and 3B illustrate conjugation of MTD to two different small molecule inhibitors of PDZ/PL interactions.

Example 5

Reduction of PSD-95 Protein Levels in Cells

PSD-95 is an important drug target for a number of disorders. To demonstrate that compound 0620-0057 can penetrate cells and affect PSD-95, this drug was added to various cell lines in vitro. Following drug addition, PSD-95 protein levels were assessed by western blotting.

Methods:
Drug tested: 0620-0057 ($C_{28}H_{45}N_3O_5$ MW=503.6880 g/mol)
10 mM stock=5.0368 mg/ml in DMSO. Stock was created by weighing out 6.70 mg of drug powder and adjusting volume to 1.33 ml of DMSO.
Cell lines tested: C33A, 293ET, A549, HCT116.
Cells were seeded at $1\times10^6$ cells/well in 6 well plate format in 3 ml of their growth media, and grown o/n at 37° C. 5% $CO_2$.
On the day of the experiment cells were washed once with 2 ml of 1×PBS
Drug solutions were prepared in 80-150 µM range from 10 mM stock solution by diluting appropriate drug amount in warm growth media.
DMSO only negative control was prepared by diluting equal volumes of TC grade DMSO in growth media same as respective drug dilutions.
3 ml/well of drug solutions and/or DMSO-only solutions were added to washed cells and cells were subsequently incubated at 37° C. for 6 h-72 hrs.

Western Blot and Probing with Anti-PSD-95 or Anti-DLG1
Lyse cells in lysis buffer (50 mM HEPES, pH 7.5, 150 mM NaCl, 1% Triton X-100, 1 mM EDTA, 10% glycerol, 1 mM phenylmethylsulfonyl fluoride, protease inhibitors (Calbiochem)).
Run samples (40 µg-150 µg of total protein lysate) in 10% SDS-PAGE minigel.
Transfer (semi-dry) to PVDF membrane (Immobilon-P, Millipore, 0.45 µm) transfer 25 Volts for 45 minutes.
Place membrane into blocking buffer TBS-T (25 mM Tris pH 7.4 with 8.77 g/l NaCl and 0.2 g/l KCl (150 mM NaCl) with 0.05 to 0.1% Tween-20) with 5% non-fat dry milk and 2% BSA. Incubate at 4° C. overnight, or 2-4 hours RT. Rinse gel with TBS-T.
Add PSD-95 monoclonal antibody (generated at AVC) or anti-DLG1 at 10 µg/ml in TBS-T. Incubate 1 hour at RT while rocking. Wash 4 times with TBS-T, for 5 minutes at RT with rocking.
Add Goat anti-mouse IgG-HRP (Jackson Immunoresearch). Wash 5 times with TBS-T, for 5 minutes at RT with rocking.
Develop with ECL Plus (Amersham) according to manufacturer's protocol. Expose to film (Kodak MR).

Conclusion:
FIG. 4 shows the results of this experiment on two cell lines. PSD-95 levels were similarly reduced in all 4 cell lines tested for compound 0620-0057. Thus, 0620-0057 has the ability to penetrate cells and without being bound by mechanism, is likely to displace cellular ligands which in turn results in the degradation of PSD-95 protein levels.

Example 6

Neuroprotective Efficacy of the Compound AVC 0620-0057 in a Mouse Model of Stroke In Vivo The neuroprotective efficacy of the AVC 0620-0057 compound was demonstrated using the in vivo pial 3 vessel occlusion (P3VO) model of stroke in mice. In addition, the neuroprotective activity of two derivatives of known neuroprotective peptides NR2B9c and Tat-NR2B9c was also tested. NR2B9c peptide sequence coupled to the Antennapedia transporter, to form the first derivative (Ac-RQIKIW-FQNRRMKWKKKLSSIESDV; Antennapedia-NR2B9c). Tat-NR2B9c was biotinylated at its N-terminus to form the second derivative.

The peptide known as Tat-NR2B9c (YGRKKRRQR-RRKLSSIESDV) has been developed and previously tested in the middle cerebral artery occlusion (MCAO) model of stroke in the rat. This peptide has been shown to be neuroprotective as seen by a reduced infarct size. However, the MCAO model of stroke results in a large infarct with extensive neurological deficits and shortened life span. The P3VO model of stroke results in a much smaller, cortical infarct with minimal neurological deficit and normal life span.

Animals

Adult Sprague Dawley rats (10-12 weeks old) (males ~300 g, females ~250 g) were fasted for 12-18 hours before being subjected to permanent pial vessel occlusion of 3 terminal branches of the Middle Cerebral Artery over the Whisker Barrel Cortex (P3VO). Each of 3 compounds were tested in male rats plus a saline control group (n=8 in each group). The researcher was blinded to the peptide treatment group during the time of surgery through to the analysis of infarct size, although the AVC 0620-0057 compound was not performed blinded due to the technique.

General Procedure

Rats were anesthetized with a 0.5 ml/kg intramuscular injection of ketamine (100 mg/kg), acepromazine (2 mg/kg), and xylazine (5 mg/kg), supplemented with one third the initial dose as required. An anal temperature probe was inserted and the animal was placed on a heating pad maintained at 37° C. The right external carotid artery (ECA) was cannulated with PE 10 polyethylene tubing for dye injections. The skull was exposed via a midline incision, scraped free of tissue, and the temporalis muscle disconnected from the skull on the right side. Using a dissecting microscope and a pneumatic dental drill, a 6×4 mm cranial window was made over the right somatosensory cortex (2 mm caudal and 5 mm lateral to bregma) by drilling a rectangle through the skull and lifting off the piece of skull while keeping the dura intact. After being bathed with artificial cerebrospinal fluid, small boluses (10 to 20 µL) of the vital dye patent blue violet (10 mmol/L; Sigma) in normal saline, were injected into the right external carotid artery to demonstrate transit through surface vessels of the cortex. Three critical arteriolar branches of the MCA around the barrel cortex were selected and electrically cauterized through the dura. After the cauterizations, the bolus injections and dye transits were repeated to ensure transits through the cauterized arterioles were blocked. The rectangle of skull was replaced over the window and the scalp was sutured. The catheter was removed from the ECA, the ECA was ligated, and the anterior neck was sutured. One hour after initiation of focal occlusion, 0.3 ml of drug (3 nMol/g body weight) or saline control were infused through the tail vein at a rate of 0.06 ml/min. For AVC 0620, a piece of sterile gelfoam was soaked with 50 uM AVC0620 and applied directly on the surface of the cauterized area. Each rat was returned to its individual cage under a heating lamp to maintain body temperature until the rat fully recovered. Food and water was supplied ad libitum.

Harvesting of Brain Tissue

Twenty-four hours post-surgery, animals were re-anesthetized with 1 mL pentobarbital and the brain was quickly harvested. One coronal slice was taken through the infarct region and incubated in 2% triphenyltetrazolium chloride (TTC) for 15 minutes at 37° C. Images were scanned and brain slices were stored at −80° C.

Analysis

Infarct size was measured as a percent of the hemisphere for each rat in the study. After obtaining infarct size measurements, the animals were separated into their respective groups. Comparisons were made between treatment groups as means±SE.

Results

As shown in FIG. 5, all three compounds show neuroprotection, and thus, are appropriate to use for any clinical indications that can be improved through the use of PSD-95 inhibitors.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 5,981,200
U.S. Pat. No. 6,942,981
U.S. Pub. US/2004/0018487
PCT Appln. PCT/US01/32202
PCT Appln. PCT/US01/44138
PCT Appln. PCT/US02/24655
PCT Appln. PCT/US03/28508
PCT Appln. PCT/US04/011195
Aarts et al., *Science*, 298:846-850, 2002.
Ausubel et al., In: *Current Protocols in Molecular Biology*, John, Wiley & Sons, Inc, New York, 1987-1999.
Avrameas et al., *Proc. Natl. Acad. Sci. USA*, 95:5601-5606, 1998.
Boukerche et al., *Cancer Res.*, 65(23):10901-10911, 2005.
Derossi et al., *J. Biol. Chem.*, 261:10444-10450, 1994.
Derossi et al., *Trends Cell Biol.*, 8:84-87, 1998.
Deval et al., *J. Biol. Chem.*, Epub Oct. 17, 2005, 2005.
Doyle, *Cell*, 95:1067-1076, 1996.
Du et al., *J. Cell Biochem.*, 94(5):1038-1045, 2005.
Elliot and D'Hare, *Cell*, 88:223-233, 1997.
Fanning & Anderson, *J. Clin. Invest.*, 103(6):767-772, 1999.
Fujihara, *EMBO J.*, 18:411-419, 1999.
Garry, *Curr. Biol.*, 13:321-8, 2003.

Hale & Marham, In: *The Harper Collins Dictionary Of Biology*, 1991.
Hampson et al., *Int. J. Oncology*, 25(5):1249-1256, 2004.
Harlow and Lane, In: *Antibodies: A Laboratory Manual*, Cold Spring Harbor Laboratory, Cold Spring Harbor, N.Y., 346-348, 1988.
Hirata et al., *Virology*, 318(1):327-336, 2004.
Kanamori et al, *J. Biol. Chem.*, 278(40):38758-38764, 2003.
Kroeger et al., *J. Biol. Chem.*, 276(16):12736-12743, 2001.
Langel, In: *Cell Penetrating Peptides*, MTS Peptides, CRC Press, Boca Rotan, 2002.
Latorre et al., *J. Cell Science*, 118(Pt. 18):4283-93, 2005.
Nagahara et al., *Nat. Med.* 4:1449-1452, 1998.
Niv and Weinstein, *J. Am. Chem. Soc.*, 127(40):14072-14079, 2005.
Pooga et al., *FASEB J.*, 12:67-77, 1998.
Ramsay et al., *Br. J. Pharmacology*, 133:315-323, 2001.
Remington's Pharmaceutical Sciences, 18th Ed. Mack Printing Company, 1289-1329, 1990.
Roche, *Trends Neurosci.*, 12:699-700, 2004.
Sambrook et al., In: *DNA microaarays: a molecular cloning manual*, Cold Spring Harbor Laboratory Press, Cold Spring Harbor, N.Y., 1989.
Sambrook et al., In: *DNA microaarays: a molecular cloning manual*, Cold Spring Harbor Laboratory Press, Cold Spring Harbor, N.Y., 2000.
Sattler, *Science*, 284(5421):1845-8, 1999.
Shibata et al., *Hepatology*, 38(1):178-186, 2003.
Singleton et al., In: *Dictionary of Microbiology and Molecular Biology*, $2^{nd}$ Ed., 1994.
Songyang et al., *Science*, 275 (5296):73-77, 1997.
Tao et al., *Neuroscience*, 117:731-9, 2003.
Vives et al., *J. Biol. Chem.* 272:16010-16017, 1997.
Walker, In: *The Cambridge Dictionary Of Science And Technology*, 1988.
Winnacker, In: *From Genes To Clones*, VCH Publishers, NY, 1987.
Xie et al., *Blood* Epub, Nov. 1, 2005.
Xu et al., *Proc. Natl. Acad. Sci. USA*, 96(1):151-156, 1999.
Yao, *Neuron*, 41:625-38, 2004.

---

The invention claimed is:

1. A method of treating stroke or traumatic brain injury comprising administering an effective amount of a compound to a subject having or predisposed to stroke or traumatic brain injury, wherein the compound is selected from:

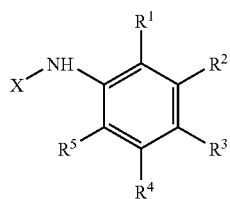

wherein one of $R^1$, $R^2$, $R^3$, $R^4$, and $R^5$ is —COOH, and wherein the remainder of $R^1$, $R^2$, $R^3$, $R^4$, and $R^5$ are selected from the group consisting of F, H, $OCH_3$ and $CH_3$; and X is -A-B-C-D-E, wherein A, B, C, D and E are connected through single bonds and A is C=O;

B is CH2;

C is C=O;

D is N—H; and

E is —NH—$COR^{14}$, wherein $R^{14}$ is $(CR^{15}R^{16})_vH$, wherein v=17 and $R^{15}$ and $R^{16}$ are H, or pharmaceutically acceptable salts thereof.

2. The method of claim 1, wherein the compound is

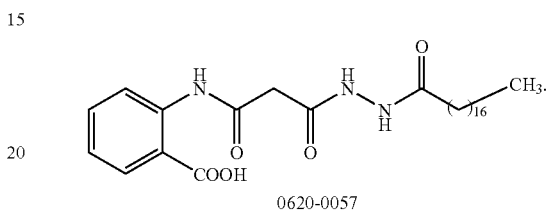

0620-0057

3. The method of claim 1, wherein the compound inhibits specific binding of PSD95 to NMDRA2B.

4. The method of claim 1, wherein the subject has stroke.

5. The method of claim 1, wherein the dose of the compound is 0.01-5 μmol/kg patient body weight.

6. The method of claim 5, wherein the dose of the compound is 0.1-1 μmol/kg patient body weight.

7. The method of claim 5, wherein the dose of the compound is about 0.5 μmol/kg patient body weight.

8. The method of claim 1, wherein the compound is administered within 6 hours of onset of the stroke or traumatic brain injury.

9. The method of claim 1, wherein the compound is administered once to the subject.

10. The method of claim 1, wherein the compound is mixed with a pharmaceutical excipient as a pharmaceutical composition.

11. The method of claim 1 wherein the subject is human.

* * * * *

UNITED STATES PATENT AND TRADEMARK OFFICE
CERTIFICATE OF CORRECTION

PATENT NO. : 8,633,160 B2  
APPLICATION NO. : 12/167852  
DATED : January 21, 2014  
INVENTOR(S) : Michael P. Belmares et al.

Page 1 of 1

It is certified that error appears in the above-identified patent and that said Letters Patent is hereby corrected as shown below:

<u>Title page</u>, Related U.S. Application Data

"(60) Provisional application No. 60/947,883, filed Jul. 3, 2007, provisional application No. 60/693,988, filed Jun. 23, 2005, provisional application No. 60/755,315, filed Dec. 30, 2005."

should read

-- (60) Provisional application No. 60/947,883, filed Jul. 3, 2007, provisional application No. 60/755,315, filed Dec. 30, 2005. --

Signed and Sealed this  
Sixth Day of May, 2014

Michelle K. Lee  
*Deputy Director of the United States Patent and Trademark Office*